(12) United States Patent
Dymock et al.

(10) Patent No.: US 8,980,873 B2
(45) Date of Patent: *Mar. 17, 2015

(54) 11-(2-PYRROLIDIN-1-YL-ETHOXY)-14,19-DIOXA-5,7,26-TRIAZA-TETRACYCLO [19.3.1.1(2,6).1(8,12)]HEPTACOSA-1(25),2(26),3,5,8,10,12(27),16,21,23-DECAENE CITRATE SALT

(75) Inventors: Brian Dymock, Singapore (SG); Cheng H. Lee, Singapore (SG); Anthony D. William, Singapore (SG)

(73) Assignee: CTI Biopharma Corp., Seattle, WA (US)

( * ) Notice: Subject to any disclaimer, the term of this patent is extended or adjusted under 35 U.S.C. 154(b) by 158 days.

This patent is subject to a terminal disclaimer.

(21) Appl. No.: 13/133,297

(22) PCT Filed: Dec. 9, 2009

(86) PCT No.: PCT/SG2009/000473
§ 371 (c)(1),
(2), (4) Date: Aug. 22, 2011

(87) PCT Pub. No.: WO2010/068181
PCT Pub. Date: Jun. 17, 2010

(65) Prior Publication Data
US 2011/0294831 A1  Dec. 1, 2011

Related U.S. Application Data

(60) Provisional application No. 61/121,668, filed on Dec. 11, 2008.

(51) Int. Cl.
*C07D 498/04* (2006.01)
*C07D 201/10* (2006.01)

(52) U.S. Cl.
CPC ............ *C07D 201/10* (2013.01); *C07D 498/04* (2013.01)
USPC .......................................... 514/183; 540/469

(58) Field of Classification Search
None
See application file for complete search history.

(56) References Cited

FOREIGN PATENT DOCUMENTS

WO    WO-2007/058627 A1    5/2010

OTHER PUBLICATIONS

Leicht. Biochimica et Biophysica Acta, 2007, 1773, 1196-1212.*
Stahl. Handbook of Pharmaceutical Salts, 2002, 278-279 and 292-293.*
Notification Concerning Transmittal of Copy of International Preliminary Report on Patentability, International Preliminary Report on Patentability and the Written Opinion of the International Searching Authority issued Jun. 23, 2011 in corresponding International Appln No. PCT/SG2009/000473.
Chinese Office Action, issued in parallel Chinese Application No. 200980150325.5 on May 31, 2013.
Israeli Office Action in Hebrew, issued in Israeli Patent Application No. 213418, dated Sep. 29, 2014.
The Israeli agent letter reporting the Israeli Office Action in Israeli Patent Application No. 213418.
D. J. W. Grant (chapter 1) p. 1-10; and J. K. Guillory (chapter 5) p. 183-226, "Polymorphism in pharmaceutical solids" edited by H. G. Brittain, Marcel Dekker, (1999).
S. Byrn et al., "Pharmaceutical Solids: A Strategic Approach to Regulatory Considerations", Pharmaceutical Research, (1995), vol. 12, No. 7, p. 945-954.
Philip L. Gould, "Salt Selection for Basic Drugs", International Journal of Pharmaceutics, (1986), vol. 33, p. 201-217.
Abu T. M. Serajuddin, "Salt formation to improve drug solubility", Advanced Drug Delivery Reviews, vol. 59, 2007, p. 603-616.
P. Heinrich Stahl, "Preparation of water-soluble compounds through salt formation", The Practice of Medicinal Chemistry, 2nd ed. 2003, p. 601-615.

* cited by examiner

*Primary Examiner* — Noble Jarrell
(74) *Attorney, Agent, or Firm* — Novak Druce Connolly Bove + Quigg LLP

(57) ABSTRACT

The present invention relates to certain salts of a 11-(2-pyrrolidin-1-yl-ethoxy)-14,19-dioxa-5,7,26-triaza-tetracyclo [19.3.1.1(2,6).1(8,12)]heptacosa-1(25),2(26),3,5,8,10,12 (27),16,21,23-decaene (Compound I) which have been found to have improved properties. In particular the present invention relates to the citrate salt of this compound. The invention also relates to pharmaceutical compositions containing the citrate salt and methods of use of the citrate salt in the treatment of certain medical conditions.

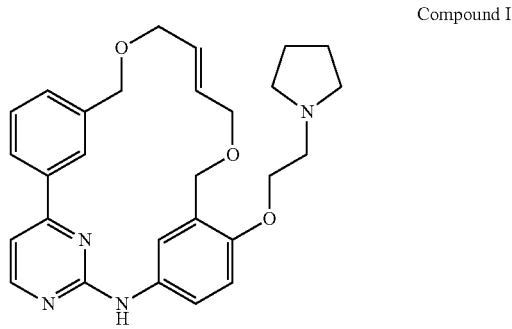

Compound I

13 Claims, 26 Drawing Sheets

Top = EtOH (20 vols)
Bottom = MeOH (10 vols)

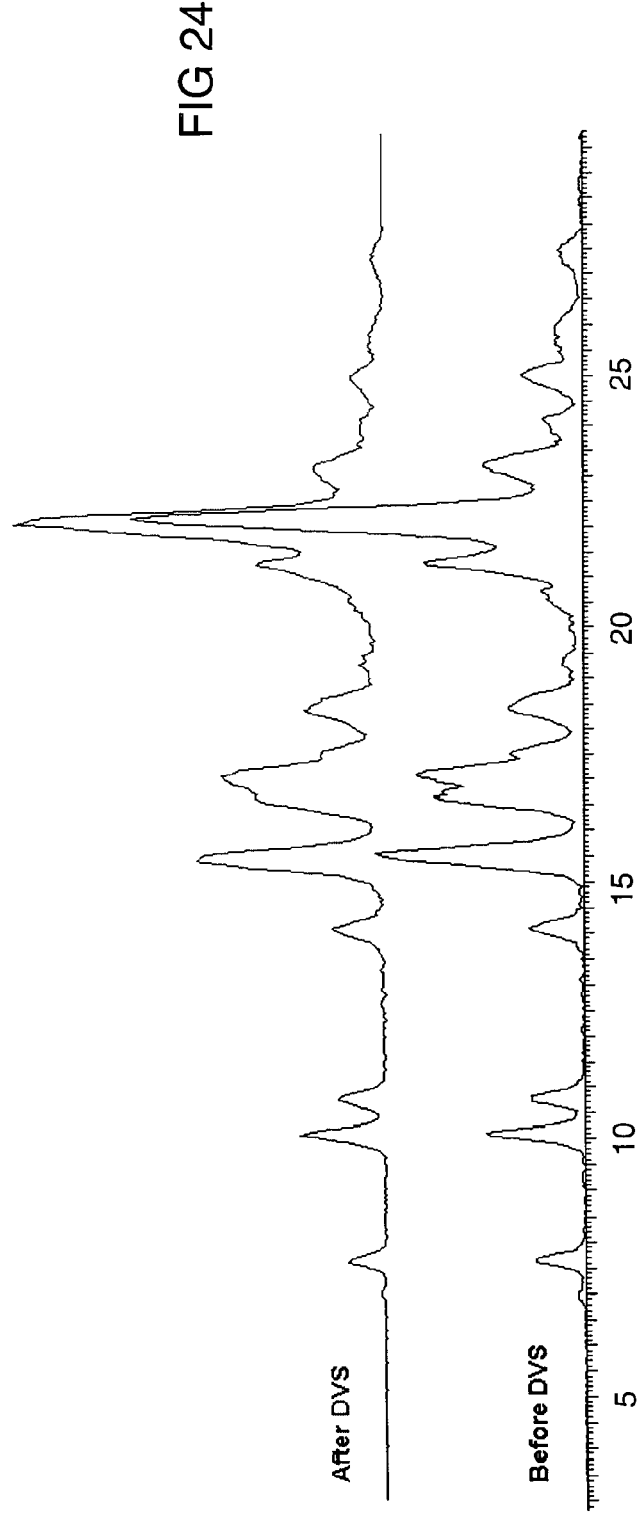
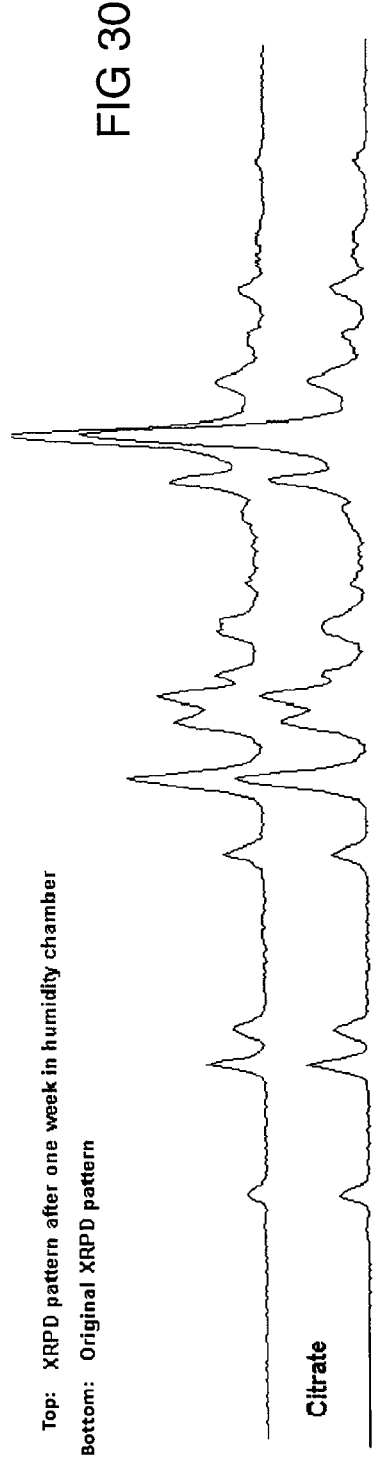

11-(2-PYRROLIDIN-1-YL-ETHOXY)-14,19-DIOXA-5,7,26-TRIAZA-TETRACYCLO [19.3.1.1(2,6).1(8,12)]HEPTACOSA-1(25),2(26),3,5,8,10,12(27),16,21,23-DECAENE CITRATE SALT

CROSS REFERENCE TO RELATED APPLICATIONS

This application is a National Phase filing under 35 U.S.C. §371 of PCT/SG2009/000473 filed on Dec. 9, 2009; and this application claims priority to U.S. Provisional Application No. 61/121,668 filed on Dec. 11, 2008 under 35 U.S.C. §119; the entire contents of all are hereby incorporated by reference.

FIELD

The present invention relates to the citrate salt of 11-(2-pyrrolidin-1-yl-ethoxy)-14,19-dioxa-5,7,26-triaza-tetracyclo[19.3.1.1(2,6).1(8,12)]heptacosa-1(25),2(26),3,5,8,10,12 (27),16,21,23-decaene. In addition the present invention relates to pharmaceutical compositions containing the citrate salt and methods of use of the salt in the treatment of certain medical conditions.

BACKGROUND

The compound 11-(2-pyrrolidin-1-yl-ethoxy)-14,19-dioxa-5,7,26-triaza-tetracyclo[19.3.1.1(2,6).1(8,12)]heptacosa-1(25),2(26),3,5,8,10,12(27),16,21,23-decaene (Compound I) was first described in PCT/SG2006/000352 and shows significant promise as a pharmaceutically active agent for the treatment of a number of medical conditions and clinical development of this compound is underway based on the activity profiles demonstrated by the compound.

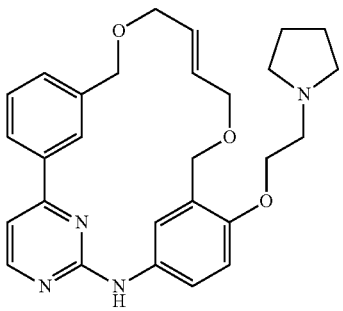

Compound I

In the development of a drug suitable for mass production and ultimately commercial use acceptable levels of drug activity against the target of interest is only one of the important variables that must be considered. For example, in the formulation of pharmaceutical compositions it is imperative that the pharmaceutically active substance be in a form that can be reliably reproduced in a commercial manufacturing process and which is robust enough to withstand the conditions to which the pharmaceutically active substance is exposed.

In a manufacturing sense it is important that during commercial manufacture the manufacturing process of the pharmaceutically active substance be such that the same material is reproduced when the same manufacturing conditions are used. In addition it is desirable that the pharmaceutically active substance exists in a solid form where minor changes to the manufacturing conditions do not lead to major changes in the solid form of the pharmaceutically active substance produced. For example it is important that the manufacturing process produce material having the same crystalline properties on a reliable basis and also produce material having the same level of hydration.

In addition it is important that the pharmaceutically active substance be stable both to degradation, hygroscopicity and subsequent changes to its solid form. This is important to facilitate the incorporation of the pharmaceutically active substance into pharmaceutical formulations. If the pharmaceutically active substance is hygroscopic ("sticky") in the sense that it absorbs water (either slowly or over time) it is almost impossible to reliably formulate the pharmaceutically active substance into a drug as the amount of substance to be added to provide the same dosage will vary greatly depending upon the degree of hydration. Furthermore variations in hydration or solid form ("polymorphism") can lead to changes in physico-chemical properties, such as solubility or dissolution rate, which can in turn lead to inconsistent oral absorption in a patient.

Accordingly, chemical stability, solid state stability, and "shelf life" of the pharmaceutically active substance are very important factors. In an ideal situation the pharmaceutically active substance and any compositions containing it, should be capable of being effectively stored over appreciable periods of time, without exhibiting a significant change in the physico-chemical characteristics of the active substance such as its activity, moisture content, solubility characteristics, solid form and the like.

In relation to 11-(2-pyrrolidin-1-yl-ethoxy)-14,19-dioxa-5,7,26-triaza-tetracyclo[19.3.1.1(2,6).1(8,12)]heptacosa-1 (25),2(26),3,5,8,10,12(27),16,21,23-decaene initial studies were carried out on the hydrochloride salt and indicated that polymorphism was prevalent with the compound being found to adopt more than one crystalline form depending upon the manufacturing conditions. In addition it was observed that the moisture content and ratio of the polymorphs varied from batch to batch even when the manufacturing conditions remained constant. These batch-to-batch inconsistencies and the exhibited hygroscopicity made the hydrochloride salt less desirable from a commercial viewpoint.

Accordingly it would be desirable to develop a salt or salts of 11-(2-pyrrolidin-1-yl-ethoxy)-14,19-dioxa-5,7,26-triaza-tetracyclo[19.3.1.1(2,6).1(8,12)]heptacosa-1(25),2(26),3,5, 8,10,12(27),16,21,23-decaene which overcome or ameliorate one or more of the above identified problems.

SUMMARY

The present invention provides a citrate salt (citric acid salt) of 11-(2-pyrrolidin-1-yl-ethoxy)-14,19-dioxa-5,7,26-triaza-tetracyclo[19.3.1.1(2,6).1(8,12)]heptacosa-1(25),2 (26),3,5,8,10,12(27),16,21,23-decaene.

In some embodiments the salt is crystalline.

In some embodiments the salt is the 1:1 citrate salt. In some embodiments the citrate salt shows on X-ray diffraction a peak on the 2theta scale at 22.4°±0.5°.

In some embodiments the citrate salt shows on X-ray diffraction peaks on the 2theta scale at 10.2°±0.5° and 15.7°±0.5°.

In some embodiments the citrate salt shows on X-ray diffraction at least four peaks on the 2theta scale selected from the group consisting of 7.8°±0.5°, 10.2°±0.5°, 14.2°±0.5°, 15.7°±0.5°, 16.8°±0.5°, 21.4°±0.5°, and 22.4°±0.5°.

In some embodiments the citrate salt shows on X-ray diffraction at least 6 peaks on the 2theta scale selected from the group consisting of 7.8°±0.5°, 10.2°±0.5°, 14.2°±0.5°, 15.7°±0.5°, 16.8°±0.5°, 21.4°±0.5°, and 22.4°±0.5°.

In some embodiments the citrate salt shows on X-ray diffraction peaks on the 2theta scale of 7.8°±0.5°, 10.2°±0.5°, 14.2°±0.5°, 15.7°±0.5°, 16.8°±0.5°, 21.4°±0.5°, and 22.4°±0.5°.

In some embodiments the citrate salt also shows on X-ray diffraction peaks on the 2theta scale of 7.2°±0.5°, 10.9°±0.5°, 17.1°±0.5°, 17.6°±0.5°, 18.5°±0.5°, 18.7°±0.5°, 20.7°±0.5°, 23.1°±0.5°, 23.3°±0.5°, 24.2°±0.5°, 25.1°±0.5°, 25.8°±0.5°, 26.2°±0.5°, 26.9°±0.5°, 27.5°±0.5°, 28.7°±0.5°, 29.3°±0.5°, 31.0°±0.5°, 32.4°±0.5°, 37.3°±0.5°, 38.6°±0.5°, 39.9°±0.5° and 41.6°±0.5°.

The present invention also provides a pharmaceutical composition comprising a salt as described above.

In another embodiment the present invention provides a method of treating or preventing a proliferative disorder comprising administration of a therapeutically effective amount of a salt of the invention to a patient in need thereof. In some embodiments the proliferative disorder is cancer.

In another embodiment the present invention provides the use of a salt of the invention in the treatment of a proliferative disorder. In some embodiments the proliferative disorder is cancer.

In another embodiment the present invention provides the use of a salt of the invention in the manufacture of a medicament for the treatment of a proliferative disorder. In some embodiments the proliferative disorder is cancer.

BRIEF DESCRIPTION OF THE DRAWINGS

FIGS. 23 and 24 show the GVS experiment and post-GVS XRPD spectra, respectively, for Batch Citrate 1.

FIG. 30 shows the X-ray diffraction pattern of the citrate salt group A material both before and after being kept for a week in the humidity chamber at 60° C. and 96% RH.

DETAILED DESCRIPTION

As stated above it has now been found that certain salts of 11-(2-pyrrolidin-1-yl-ethoxy)-14,19-dioxa-5,7,26-triazatetracyclo[19.3.1.1(2,6).1(8,12)]heptacosa 1(25), 2(26),3,5, 8,10,12 (27),16,21,23-decaene exist as single robust polymorphs. In particular the present applicants have found that the citrate salt (citric acid salt) of this compound exists as a single polymorph.

Whilst it is considered that the structure of citric acid would be clear to a skilled addressee in the art in order to avoid any uncertainty the structure is shown below.

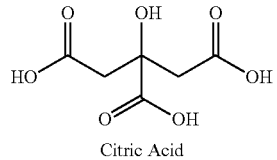 [SMILES: O=C(O)CC(O)(CC(=O)O)C(=O)O]

Citric Acid

Initial studies into compound I involved analysis of the hydrochloride salt. It was found as summarised in Table 1 below, that the initially prepared hydrochloride salt produces an inconsistent solid form with significant variability in the DSC, TGA, GVS and XRPD pattern (see FIGS. 1 to 16).

TABLE 1

Tabulation of Solid form analysis of various Hydrochloride salts of Compound 1

| Batch # | Batch Size | Solid Form Comment (see text) |
|---|---|---|
| HCl 1 | 0.72 kg | Group 1 + 3 + amorphous |
| HCl 2 | 0.6 kg | Predominately Group 1 |
| HCl 3 | 1.6 kg | Group 1 + 3 + little amorphous |
| HCl 4 | 79 mg | Group 1 |
| HCl 5 | 10 mg | Group 2 |
| HCl 6 | 30 mg | Group 3 |

As can be seen from the table notwithstanding the same production conditions (batches 1 to 3) being used there was a wide variety of solid forms identified on analysis of the 6 hydrochloride salt batches indicating that with this salt there is a high degree of polymorphism.

Figure 1:
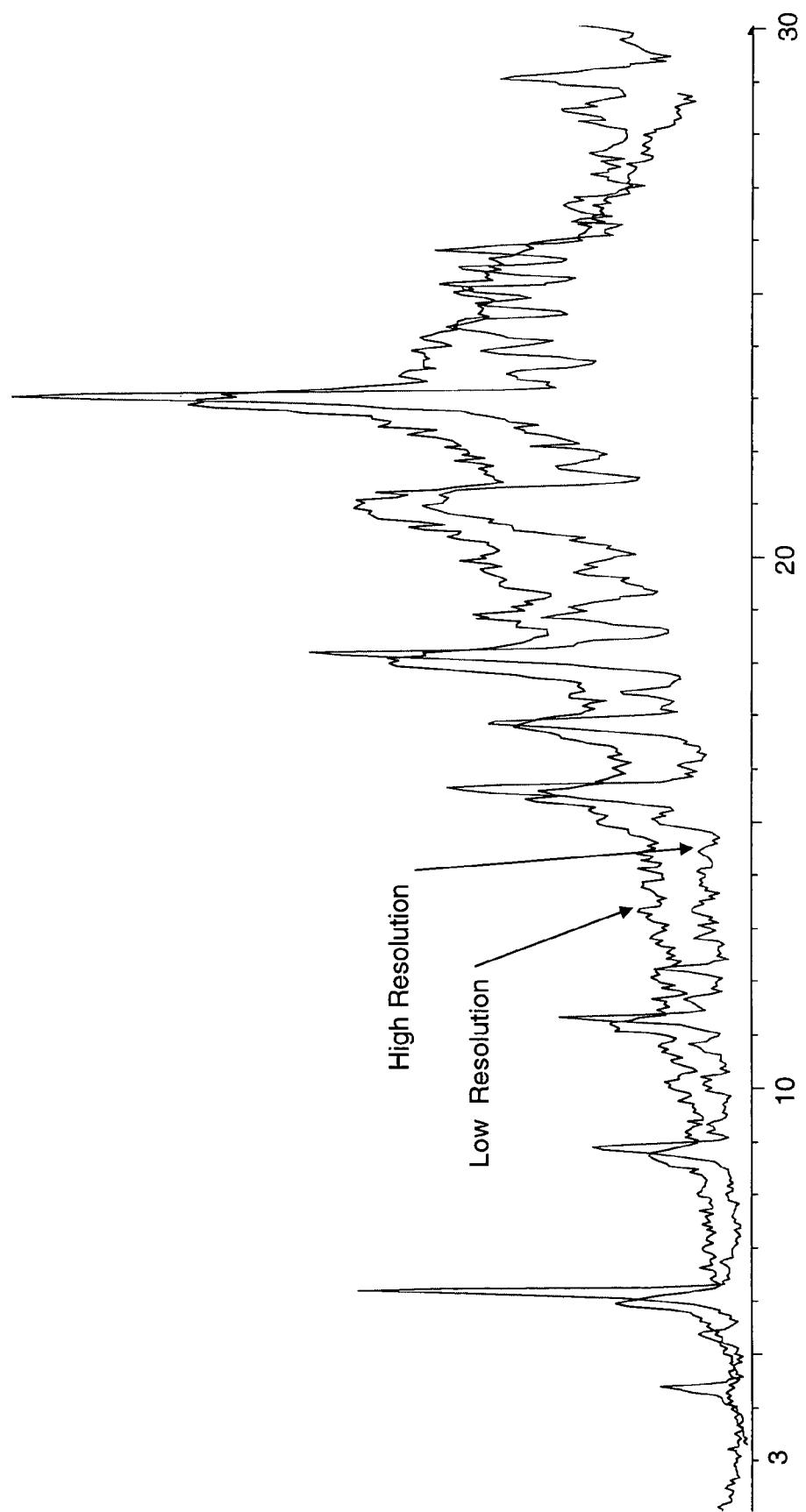
FIG. 1 shows the X-ray powder Diffraction (XRPD) Diffractogram of Batch HCl 1: low resolution trace (C2, above) and high resolution trace (D5000, below).
Figure 2:
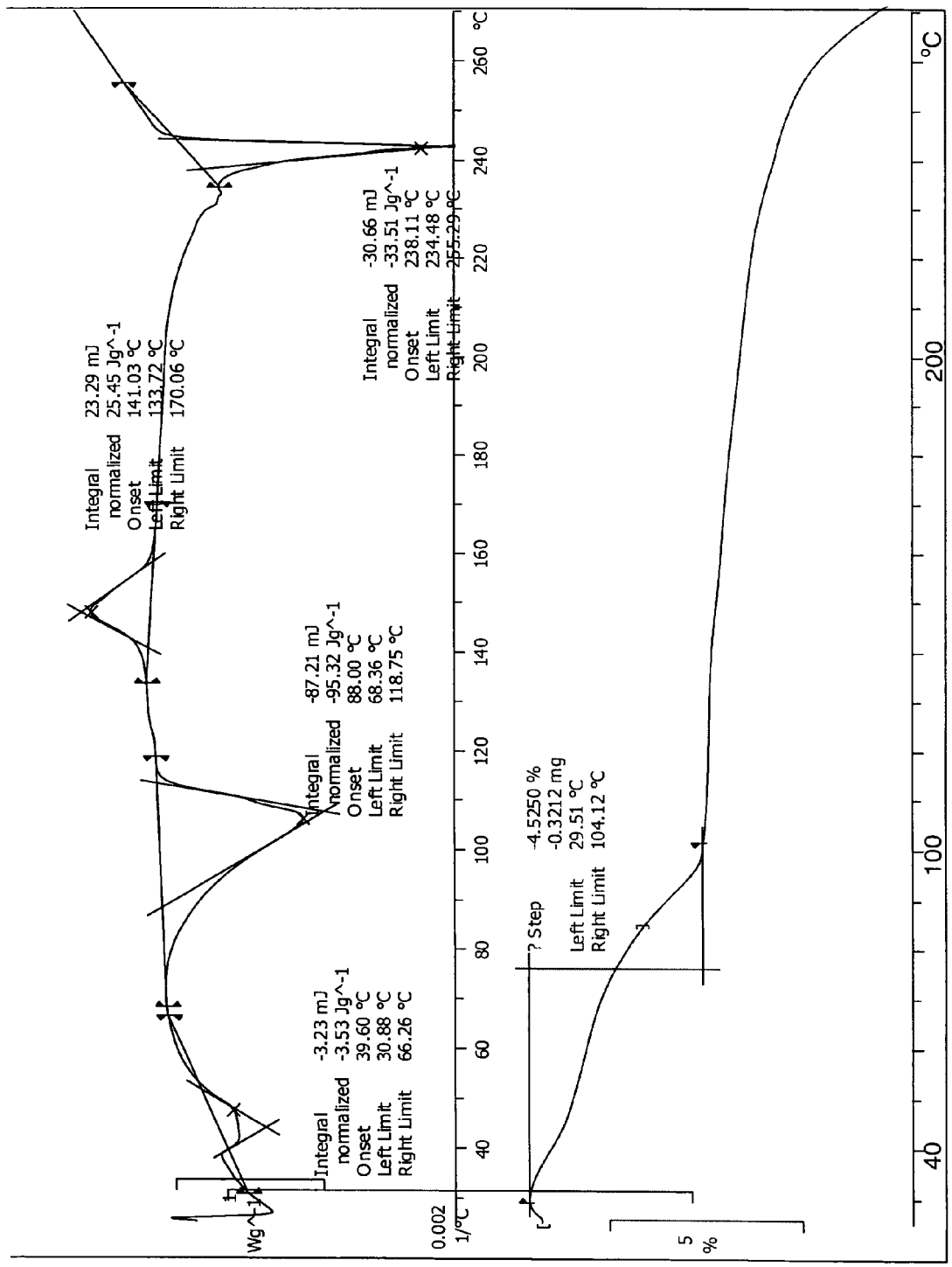
FIG. 2 shows the results of differential scanning calorimetry (DSC) (top) and thermal gravimetric analysis (TGA) (bottom) of Batch HCl 1.

The XRPD for the sample of Batch HCl 1 (see table 1) is shown in FIG. 1. This diffractogram indicates this batch has relatively low levels of crystallinity and an amorphous halo indicating a mixture of phases. The thermal gravimetric analysis (TGA) and differential scanning calorimetry (DSC) for the sample of Batch HCl 1 is shown in FIG. 2. The TGA shows a two stage weight loss totalling 4.5% up to 100° C.

which equates to 1.4 equivalents of water. This corresponds well to the two endotherms seen in the DSC with onsets of 40° C. and 88° C., respectfully. This is most likely to be a loss of water from the sample since no process solvents were observed in the $^1$H NMR. There then follows an exothermic event onset 141° C. which is most likely to be a phase change to a new solid form followed by a final endothermic event, probably a melt, onset 238° C. followed by decomposition. These physical changes can be visually seen in a hot-stage microscopy video.

Figure 3:
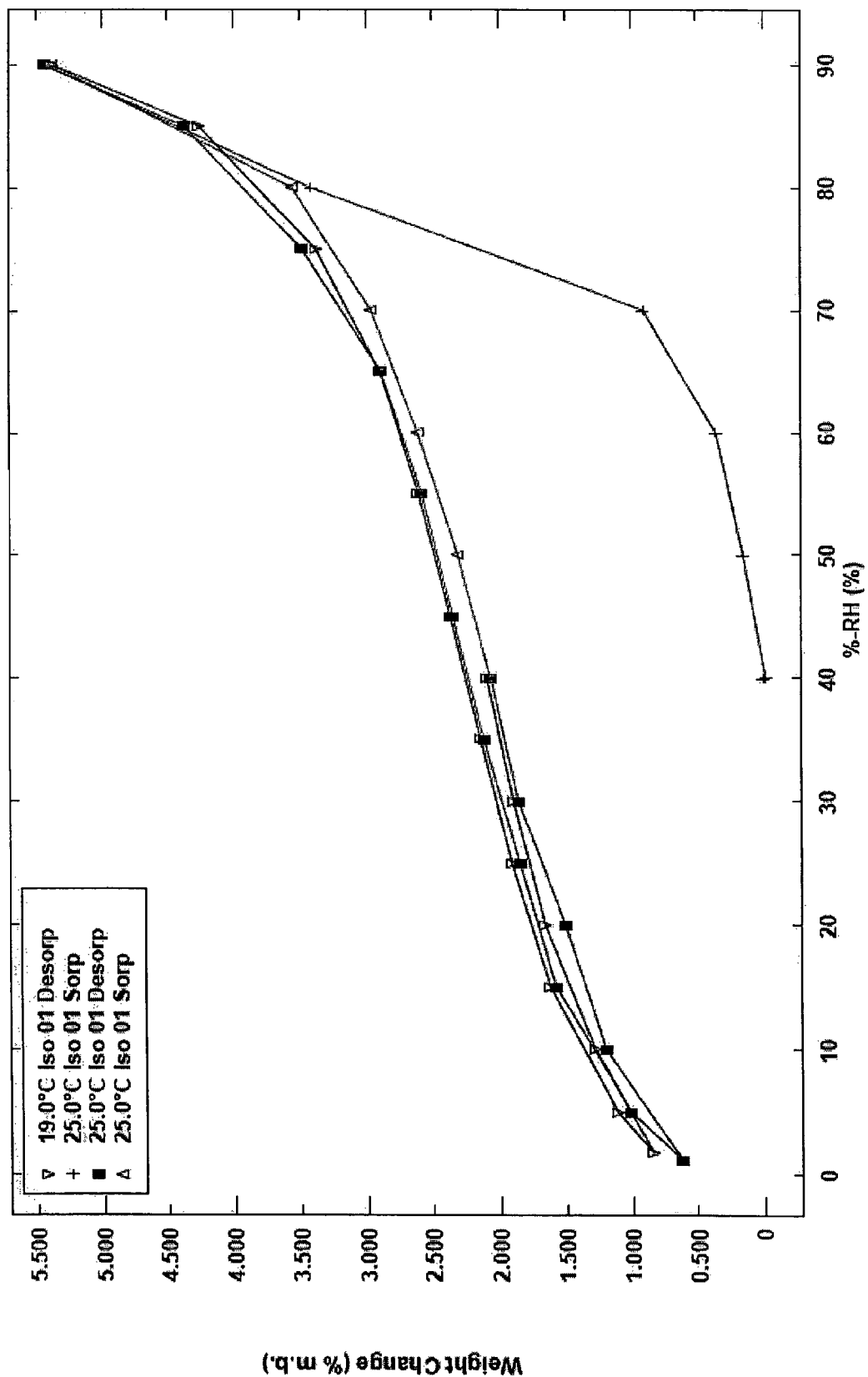
FIG. 3 shows the results of Gravimetric Vapour Sorption (GVS) of Batch HCl 1.
Figure 4:
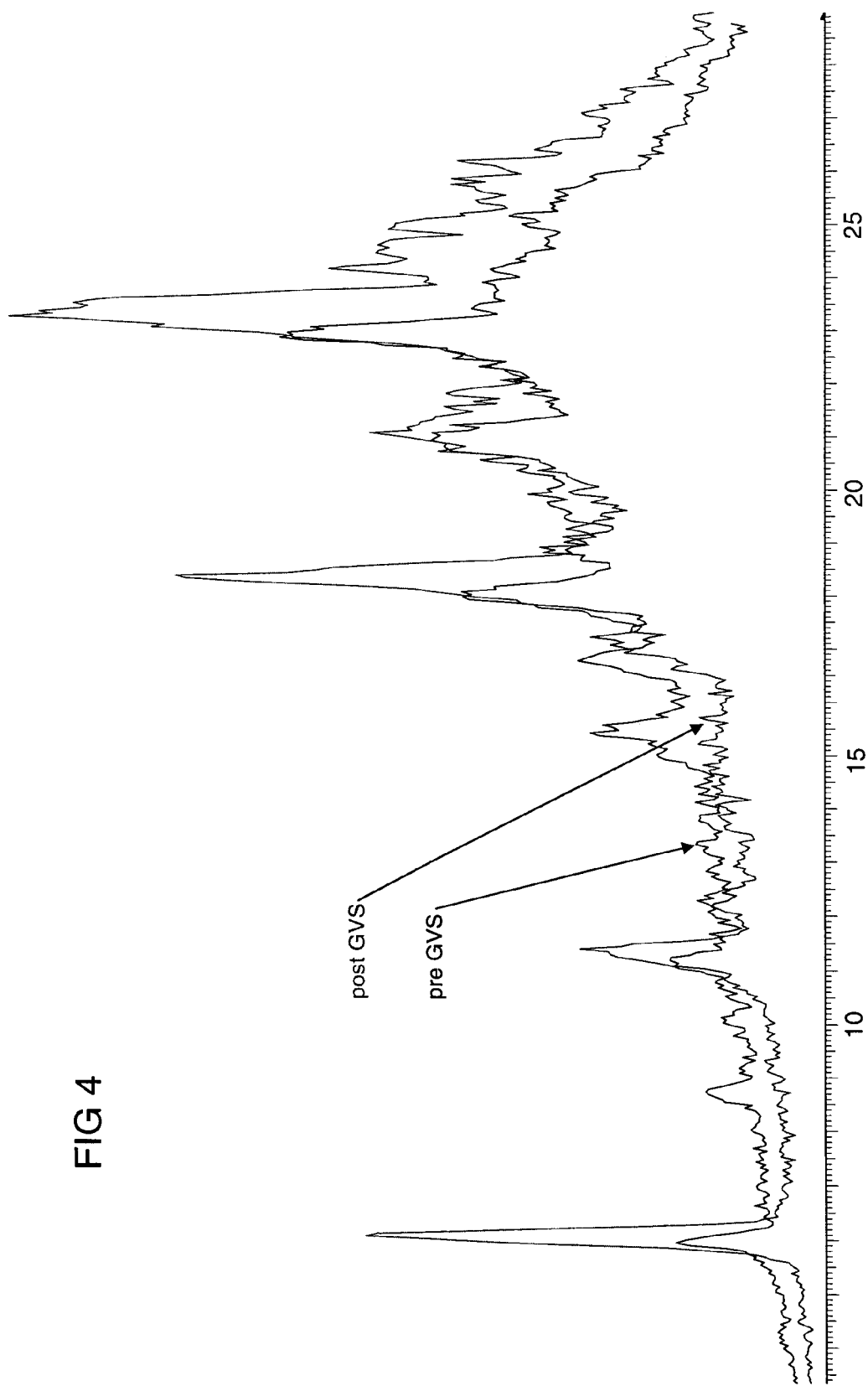
FIG. 4 shows the XRPD Diffractograms of Batch HCl 1 pre- and post-GVS.

The GVS results for the sample of Batch HCl 1 are shown in FIG. 3. The sample shows an initial adsorption of water in the initial adsorption cycle of +5.5% at 90% RH. The sample then loses 5% mass on going to dryness and then regains 2% mass on going to 40% RH with a total gain of 2%. This gain of 2% would bring the water content up to 6.5% which corresponds to a dihydrate. The sample appears to be a partially dehydrated hydrate that, once it has been exposed a high enough level of humidity gains water and then permanently holds on to it during the GVS experiment. To determine if there had been a change in the solid form of the material after the GVS experiment a XRPD diffractogram was obtained and is shown in FIG. 4. The X-ray diffractogram post GVS is similar to that of the starting material, but with more intense peaks. Also some minor peaks in the original diffractogram (ca. 8.5 and 15.5 2theta) have disappeared. It is likely that the material subjected to the GVS experiment contains more than one crystalline phase (form) and that one of the forms changes on exposure to elevated humidity.

Figure 5:
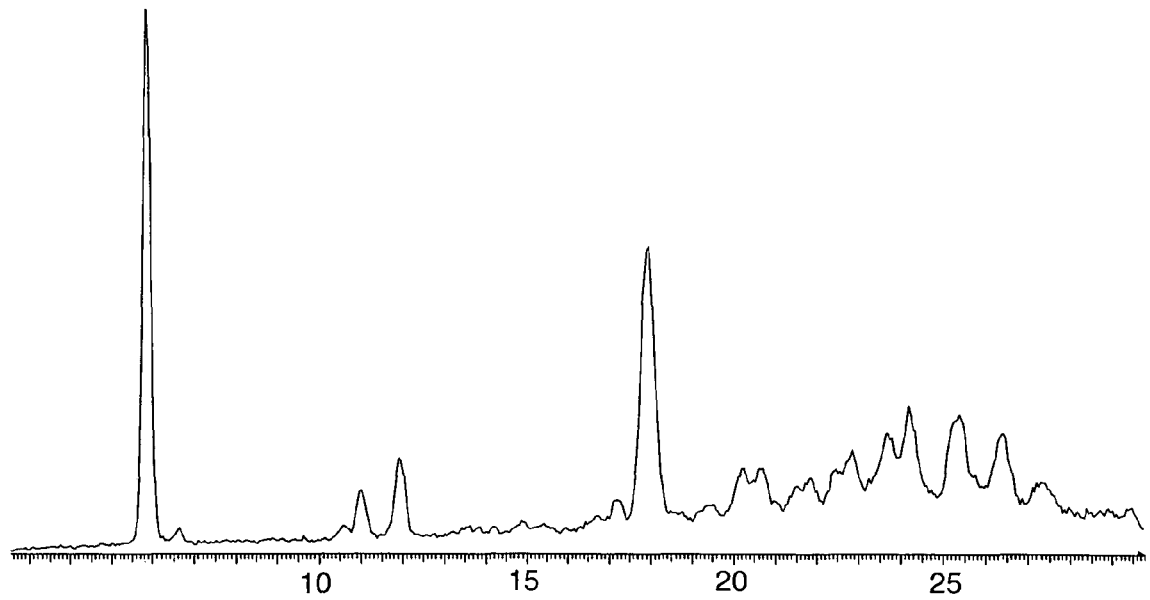
FIG. 5 shows the XRPD Diffractogram of Batch HCl 2.
Figure 6:
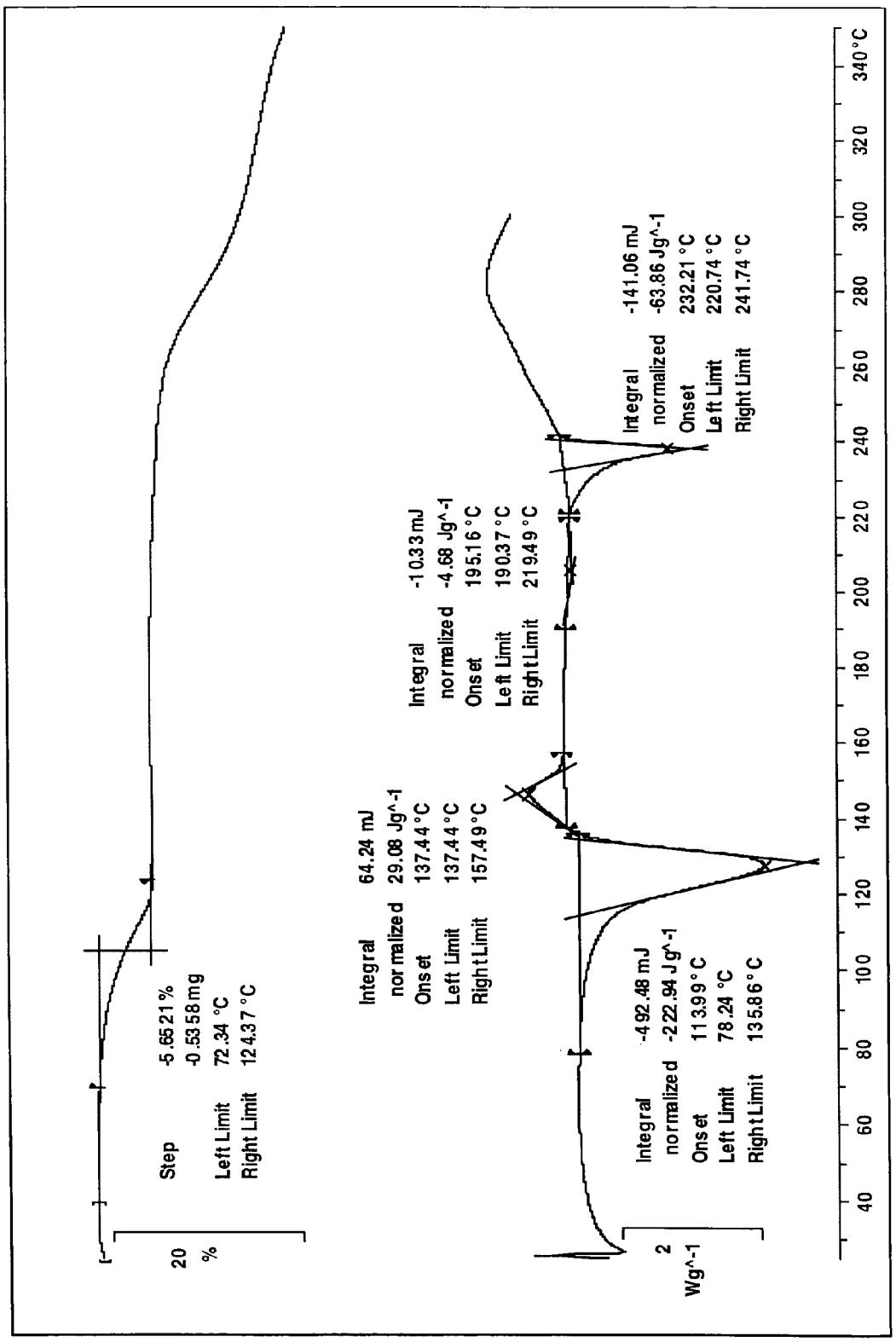
FIG. 6 shows the results of TGA (top) and DSC (bottom) of the Batch HCl 2.

The XRPD spectrum of Batch HCl 2 is shown in FIG. 5 and as can be seen there is a low correlation with the XRPD obtained with the HCl 1 batch. The TGA and DSC spectra of Batch HCl 2 are shown in FIG. 6 and have some similarities, but is not identical, to Batch HCl 1. Batch HCl 2 lost 5.6% water in the first phase of the TGA until decomposition at 260° C. This water loss represents 1.67 equivalents of water. The DSC spectrum shows the same 3 thermal events as seen with Batch HCl 1, however the two data sets are clearly not identical.

Figure 7:
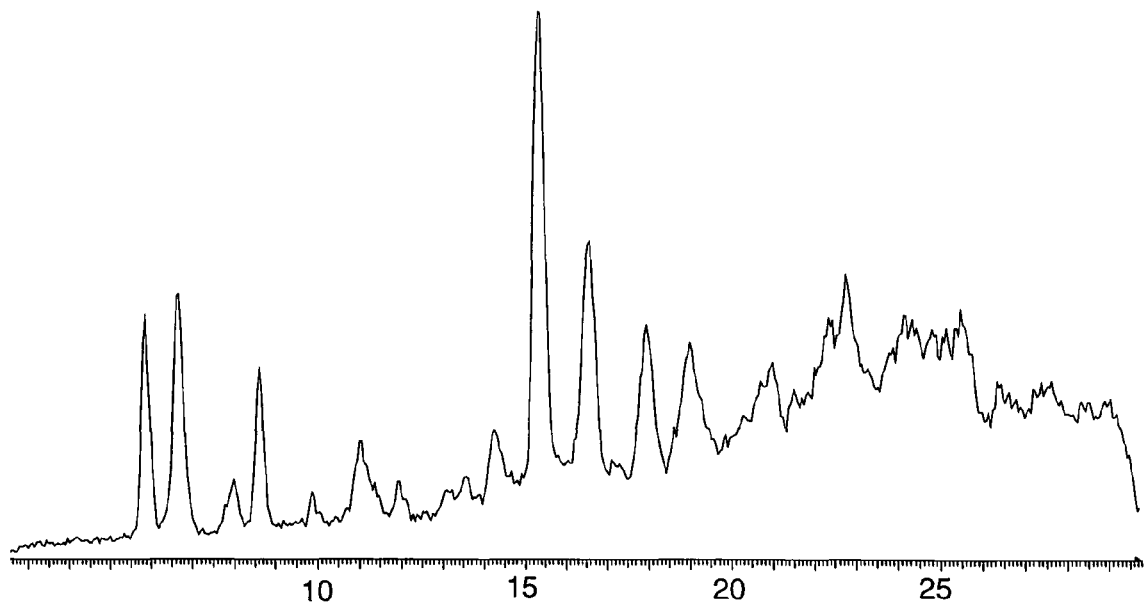
FIG. 7 shows the XRPD Diffractogram of Batch HCl 3.
Figure 8:
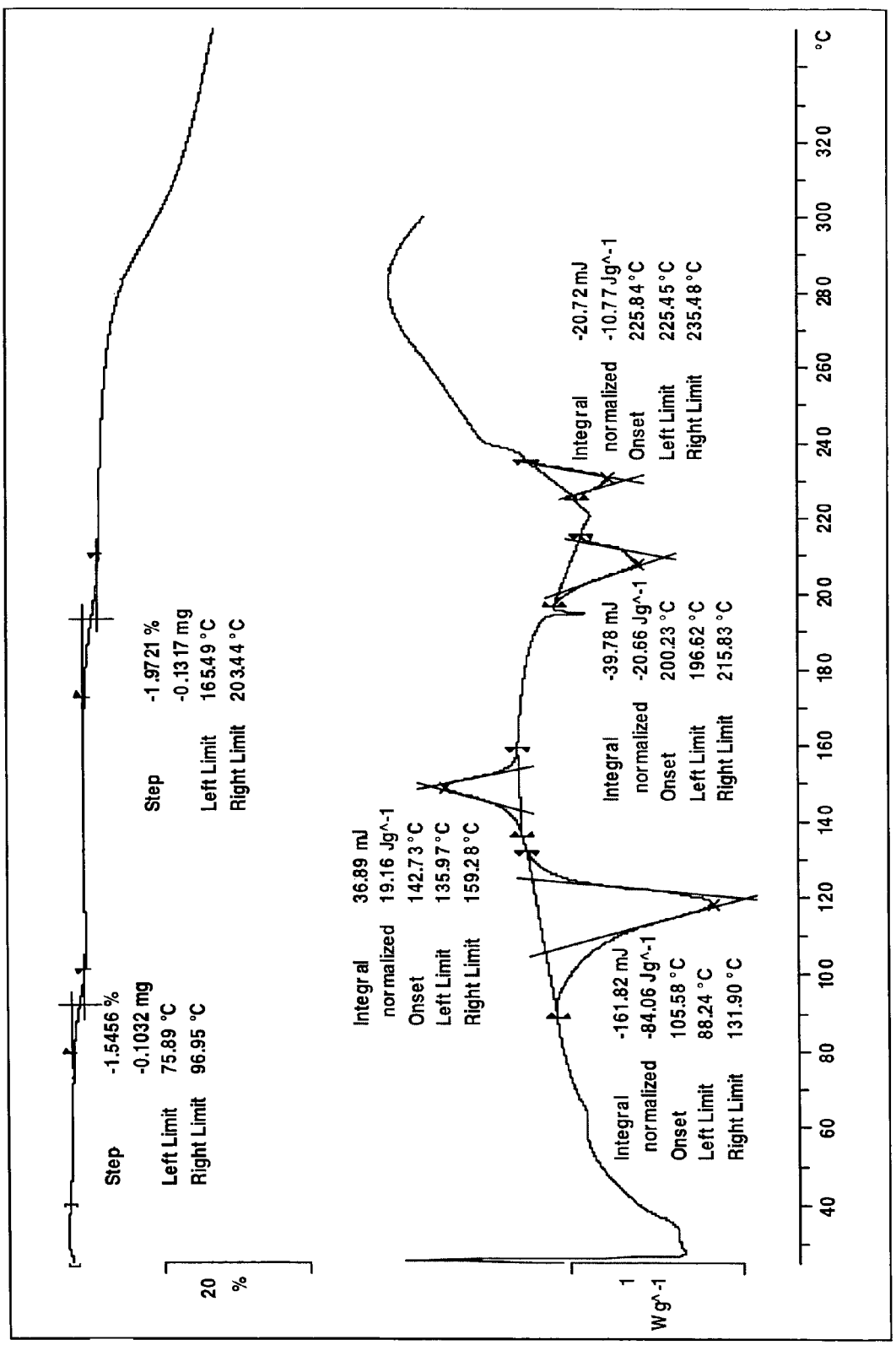
FIG. 8 shows the results of TGA (top) and DSC (bottom) of the Batch HCl 3.

The XRPD spectrum of Batch HCl 3 is shown in FIG. 7 and did not agree well with either the HCl 1 or HCl 2 batches. The XRPD of Batch HCl 3 was quite complex with many more reflections that other batches and an additional reflection at 2θ of 6.7 not present in other batches. The TGA and DSC spectra of Batch HCl 3 is shown in FIG. 8. The sample lost 1.5% water in the first phase of the TGA then another loss of 1.97%, possibly solvent, at 165° C. until decomposition at 260° C. This water loss represents 0.5 equivalents of water, lower than the 1.1 equivalents (3.79%) indicated by Karl-Fischer analysis. One possible reason for this is that a higher temperature is required to liberate the water trapped in the structure by means of dehydration, a small expansion of the lattice which will release water trapped or a change in the crystalline structure. The total weight lost in the TGA is 3.4%. The DSC spectrum shows the same 3 thermal events as seen with Batches HCl 1 and 2 but with an additional endothermic event at 200° C., probably a desolvation.

Figure 9:
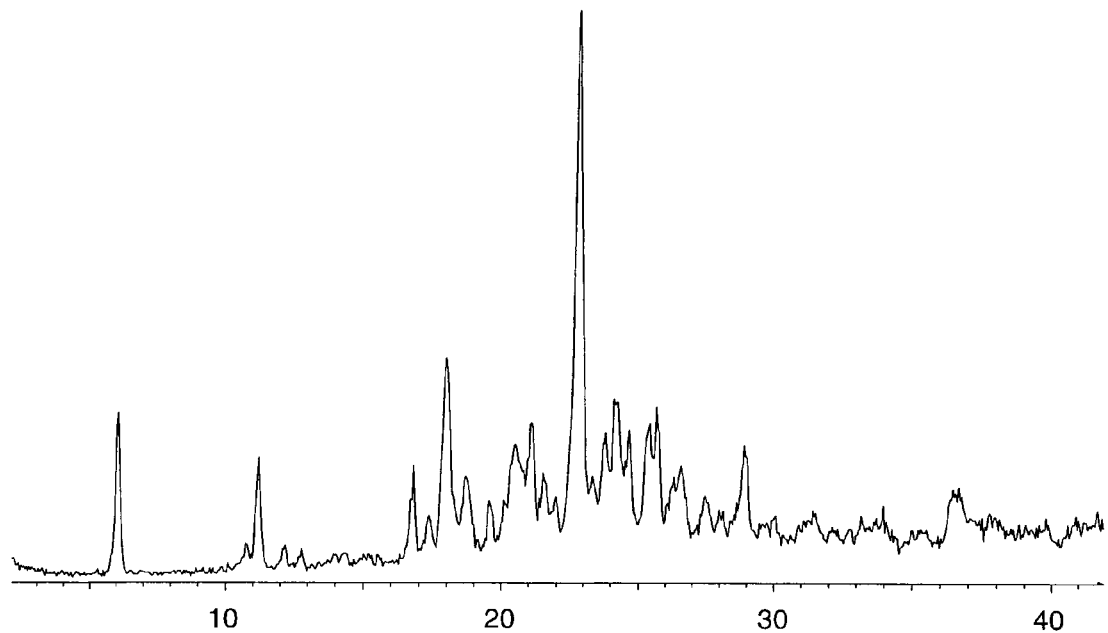
FIG. 9 shows the high resolution XRPD Diffractogram of Batch HCl 4.
Figure 10:
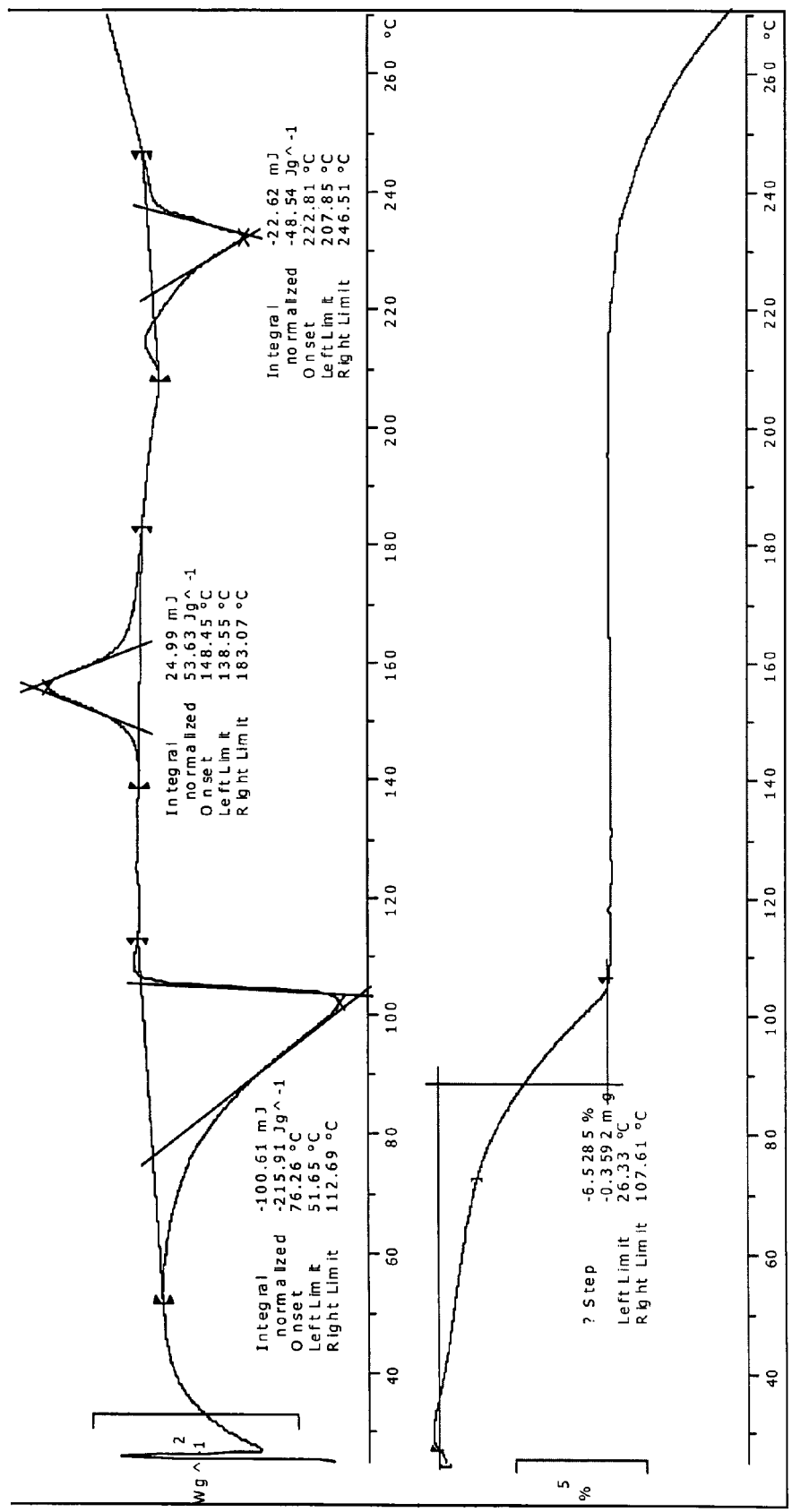
FIG. 10 shows the results of DSC (top) and TGA (bottom) of the Batch HCl 4.

In order to probe the behaviour observed above the HCl salt was recrystallised from refluxing acetonitrile/water to yield 79 mg of a yellow powder, Batch HCl 4. This was analysed by XRPD, TGA and DSC and the data is shown in FIGS. 9 and 10. This material was shown to be a single, isolable polymorphic form of the HCl salt (henceforth known as 'Group 1'). As an alternative to recrystallisation, direct formation of the Group 1 material from the free base and aqueous acid may also be accomplished. FIG. 9 which shows the XRPD spectrum of Batch HCl 4 (Group 1) did not agree well with any of the previously described batches. FIG. 10 shows the TGA and DSC spectra of Batch HCl 4 indicating that the sample loses 6.5% of its mass between ambient and 108° C. Two equivalents of water equates to 6.58%. This correlates well with the broad endotherm observed in the DSC (onset=76° C.). The DSC then shows an exothermic phase change (onset=148° C.) then goes on to show a final endotherm (onset 222° C.).

Figure 11:
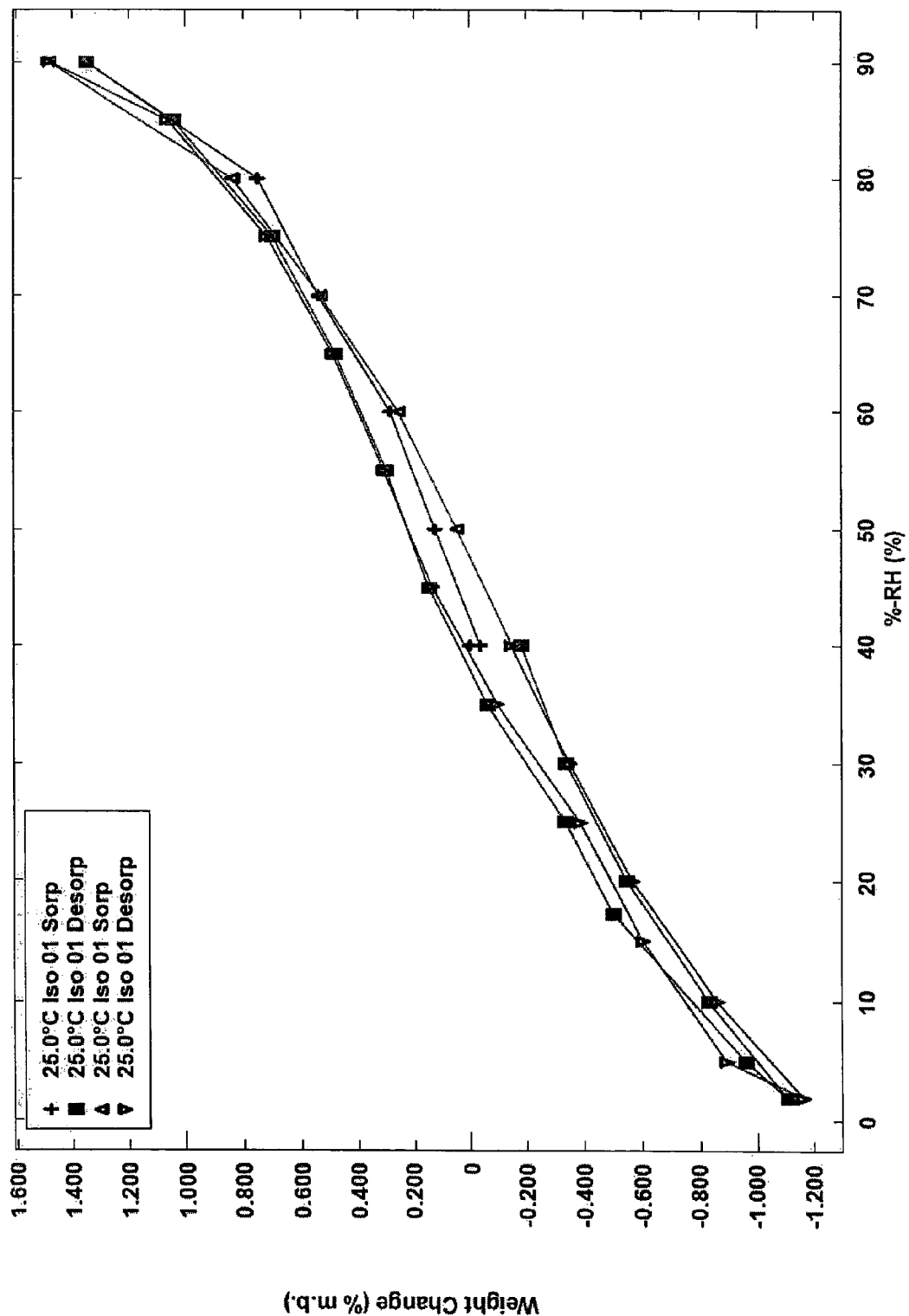
FIG. 11 shows the results of GVS of Batch HCl 4.

GVS analysis was carried out and the data is shown in FIG. 11. The sample showed very little absorption of water gaining only 1.6% mass on going from 40% RH to 90% RH. The sample lost 2.8% mass on going from 90% RH to dryness. The sample was analysed by XRPD post GVS. The form of the sample was is unchanged (data not shown).

Figure 12:
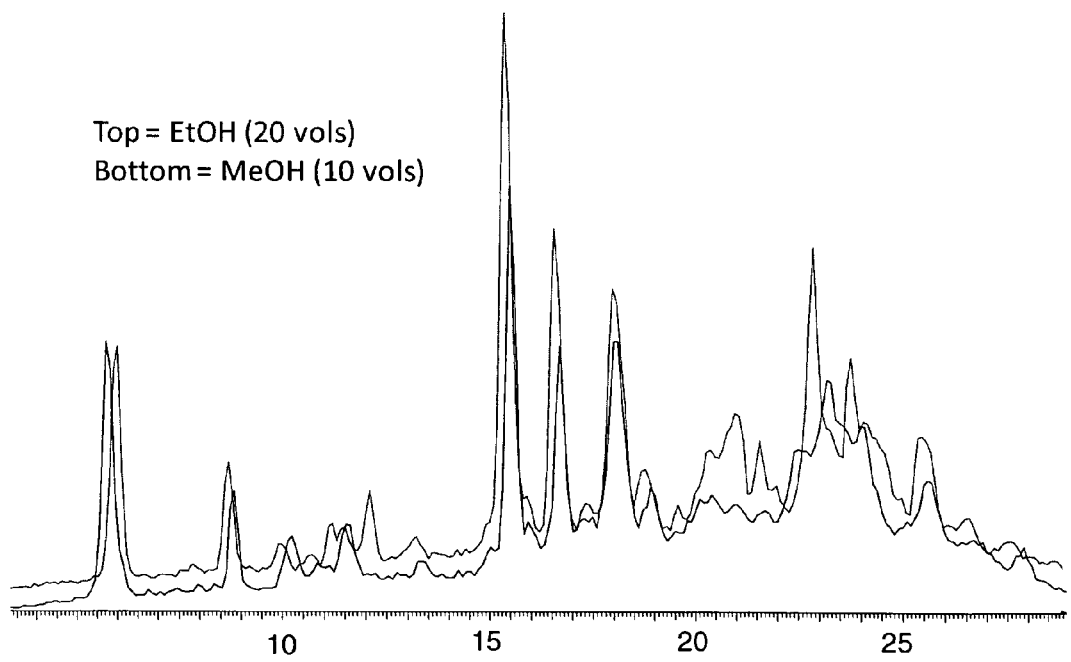
FIG. 12 shows the XRPD Diffractogram of Batch HCl 5 (2 conditions).
Figure 13:
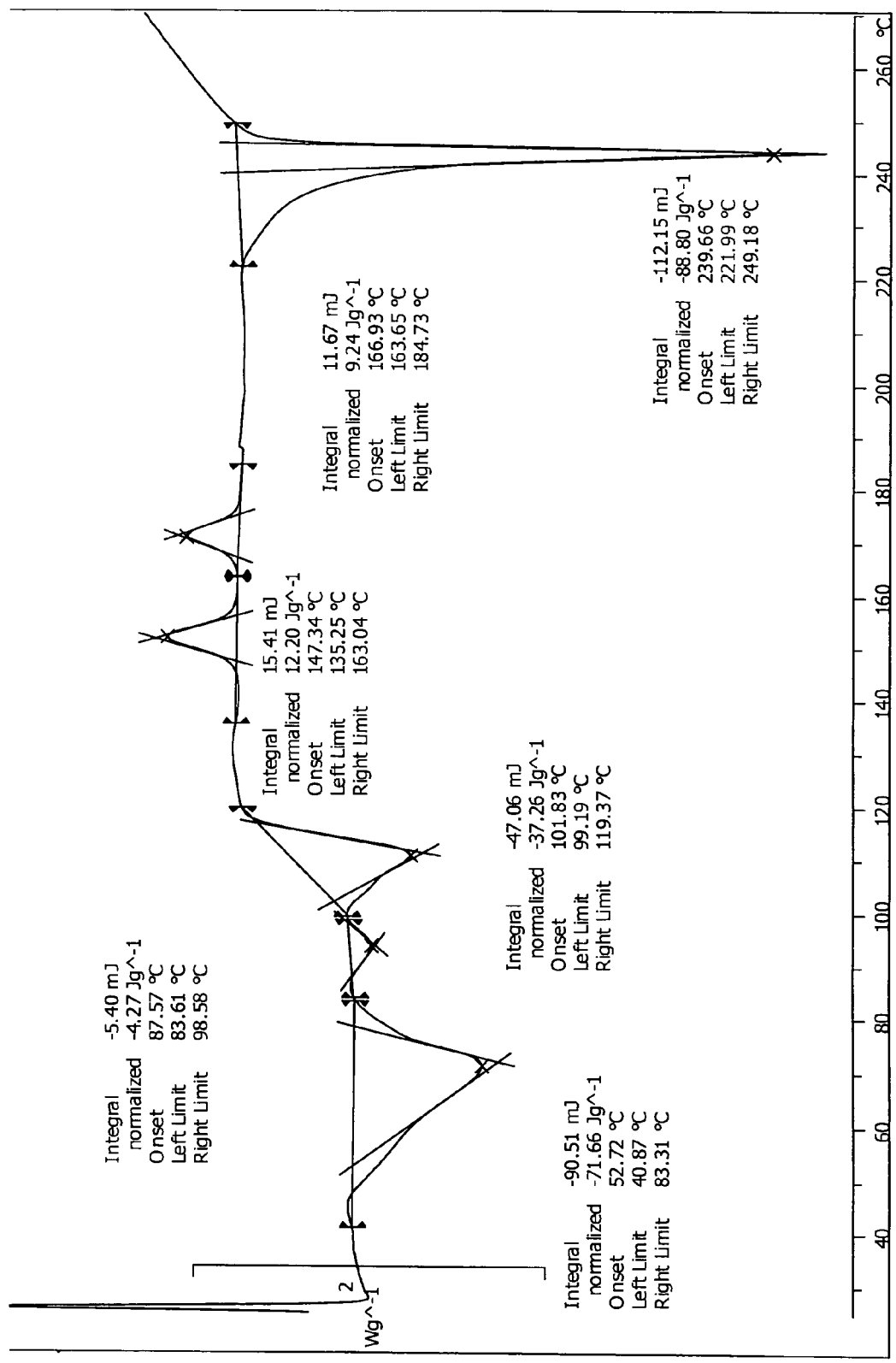
FIG. 13 shows the results of the DSC thermogram of the Batch HCl 5 (prepared from Ethanol).

A second, different, isolable polymorphic form (Batch HCl 5) may be prepared when the HCl salt is synthesised from amorphous HCl salt via a 'maturation' process. In this process a small amount of the amorphous salt (10 mg) was treated with 10 or 20 volumes of methanol or ethanol in a vial. The vials were then capped and placed in a maturation chamber that cycled from ambient to 50° C. with four hours spent under each condition. After approximately 18 hours the samples were filtered and analysed. This material was shown to be a single, polymorphic form of the HCl salt different from that of the Group 1 material (henceforth known as 'Group 2'). FIG. 12 shows the XRPD diffractograms for samples prepared in ethanol (20 vols, top) and methanol (10 vols, bottom). Although there are small differences between samples it is clear that these data are quite different from other batches described herein. FIG. 13 shows the DSC of the sample prepared in ethanol which is clearly much more complex than other batches.

Figure 14:
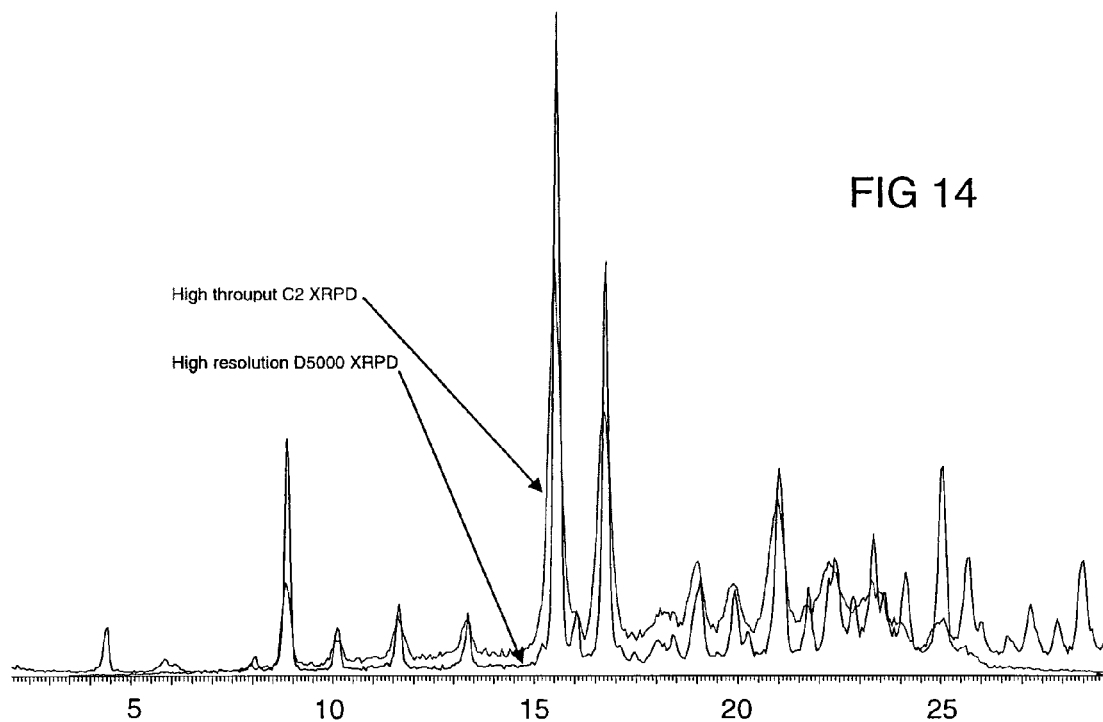
FIG. 14 shows the XRPD Diffractogram of Batch HCl 6: low resolution trace (C2, above) and high resolution trace (D5000, below).
Figure 15:
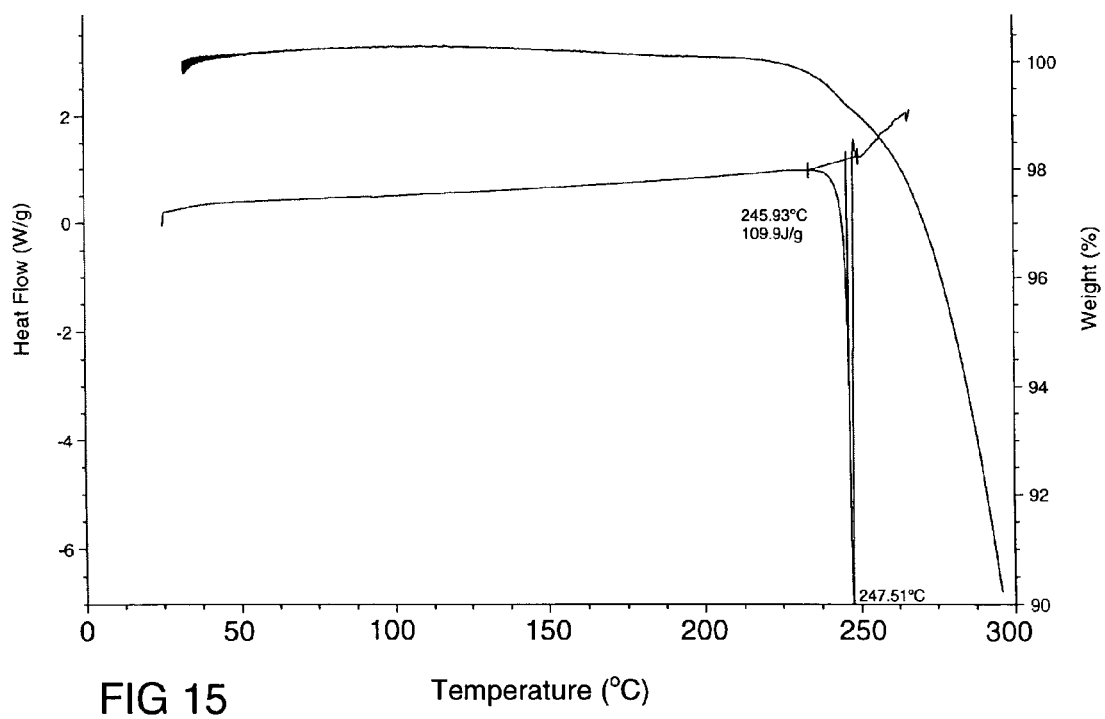
FIG. 15 shows the results of TGA (top) and DSC (bottom) of the Batch HCl 6.
Figure 16:
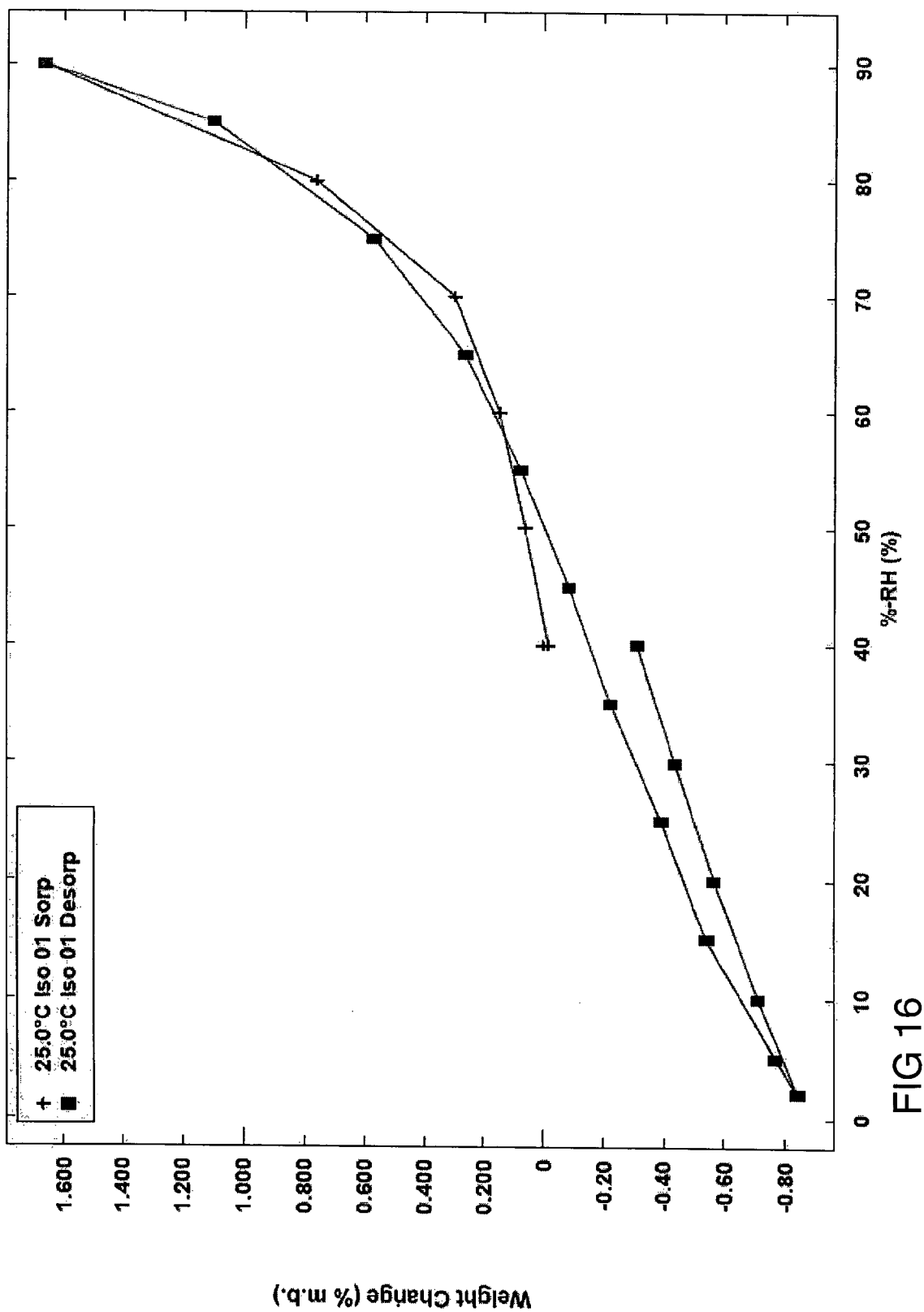
FIG. 16 shows the results of GVS of Batch HCl 6.

A third, different, isolable polymorphic form, Batch HCl 6, may be prepared when the HCl salt is synthesised from the free base in acetone or in alcoholic solvents with methanolic or aqueous HCl. FIG. 14 shows the XRPD diffractogram, recorded on low and high resolution instruments, and, again, is different from other batches described herein. Strikingly, the DSC and TGA spectra shown in FIG. 15 are very simple with very little weight loss recorded in the TGA until degradation occurs at around 240° C. and likewise no thermal events in the DSC until melting and decomposition. This material was shown to be a single, polymorphic form of the HCl salt different from that of the Group 1 and 2 materials (henceforth known as 'Group 3'). In the GVS (FIG. 16) the sample showed very little sorption of water gaining only 1.6% mass on going from 40% RH to 90% RH. The sample lost 2.4% mass on going from 90% RH to dryness. The sample was analysed by XRPD post GVS. The form of the sample was unchanged after the experiment (data not shown). Both the GVS experiments from Batches HCl 4 and 6 (Groups 1 and 3) were somewhat similar to each other but different to that of Batch HCl 1, further highlighting the variable nature of the HCl salt.

The group three material was stressed under conditions which might cause it is to convert to group one material or, indeed, another hydrated or polymorphic form. Thus samples were stored at 40° C./75% RH and also at 60° C./96% RH and analysed at regular intervals by XRPD. The results are summarised in Table 2.

TABLE 2

Tabulation of stress tests on group 3 hydrochloride

| Experiment | Conditions | Time | Comment |
|---|---|---|---|
| 1 | 40° C./75% RH | 0 hrs | Group three |
| 2 | 60° C./96% RH | 0 hrs | Group three |
| 3 | 40° C./75% RH | 24 hrs | Group three |

TABLE 2-continued

Tabulation of stress tests on group 3 hydrochloride

| Experiment | Conditions | Time | Comment |
|---|---|---|---|
| 4 | 60° C./96% RH | 24 hrs | Group one |
| 5 | 40° C./75% RH | 48 hrs | Group three |
| 6 | 40° C./75% RH | 72 hrs | Group one |

From the XRPD data (not shown) it would appear that the group three material can convert into the group one material at elevated temperature and humidity. This would have implications if the group three material was chosen as the preferred form for production as it would need to be produced in a controlled fashion and any post production manipulations, such as the formulation method, would need to be controlled to ensure that it would not convert into the group one material.

In summary, the processes employed to prepare and purify 11-(2-pyrrolidin-1-yl-ethoxy)-14,19-dioxa-5,7,26-triaza-tetracyclo[19.3.1.1(2,6).1(8,12)]heptacosa-1(25),2(26),3,5, 8,10,12(27),16,21,23-decaene HCl salt are not adequately controlling the polymorphic form of the compound as there is significant batch to batch variation observed. Despite careful work to identify 3 different apparently isolable solid forms (Batches HCl 4-6) it is quite clear that the larger scale batches produced (HCl 1-3) do not closely match any of these reference standards. Batches HCl 1 and 3 are both mixtures of Groups 1 and 3 forms with varying quantities of amorphous content. Batch HCl 2 is quite close to Group 1 but unfortunately contains other unexplained peaks in the XRPD pattern. In addition even when a single polymorph is produced (batches 4 to 6) these still exhibit significant water absorption (typically up to 1.6%) which makes their use in pharmaceutical formulations difficult to ensure consistent dosing. In addition the most promising of the hydrochloride salts (batch HCl 6—group 3) from the standpoint of the DSC analysis has been found to convert to other is polymorphic forms under stress as discussed above indicating that this is not a stable polymorph.

As a result of the unacceptable variability observed with the hydrochloride salt as discussed above an alternative robust solid form was required. Further discovery endeavours identified the citrate salt as being one such robust solid form. Table 3 lists the batches of citrate salt prepared and analysed.

TABLE 3

| Batch # | Batch Size | Solid Form Comment |
|---|---|---|
| Citrate 1 | 0.3 g | Group A |
| Citrate 2 | 20 g | Group A |
| Citrate 3 | 66 g | Group A |
| Citrate 4 | 37 g | Group A |
| Citrate 5 | 3.5 kg | Group A |
| Citrate 6 | 0.88 kg | Group A |

Analysis of the various batches of the citrate salt referred to in the table above demonstrated remarkable consistency as a single polymorph.

Figure 17:
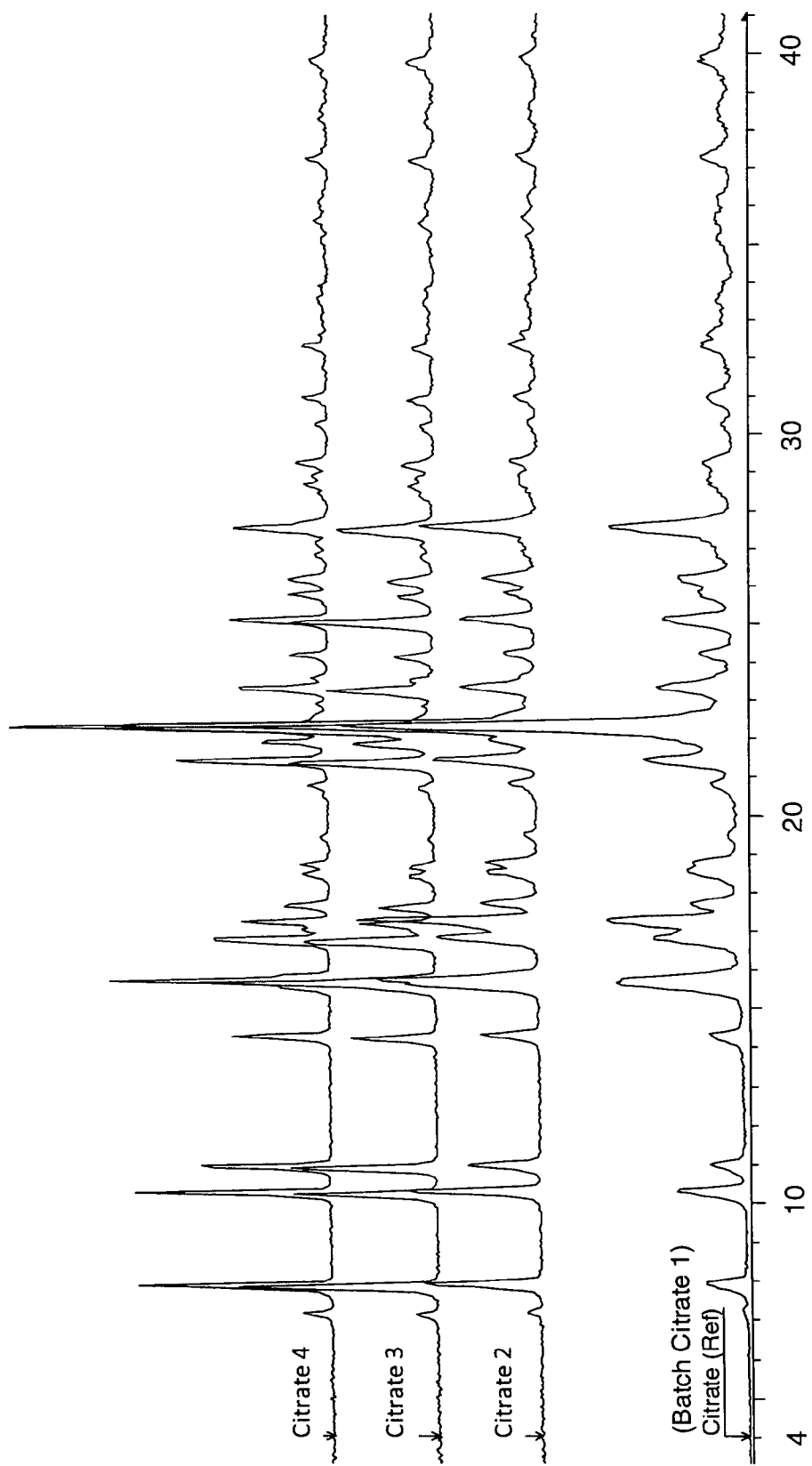
FIG. 17 shows the high resolution X-ray diffraction patterns (D5000) of Batches Citrates 1, 2, 3 and 4.
Figure 18:
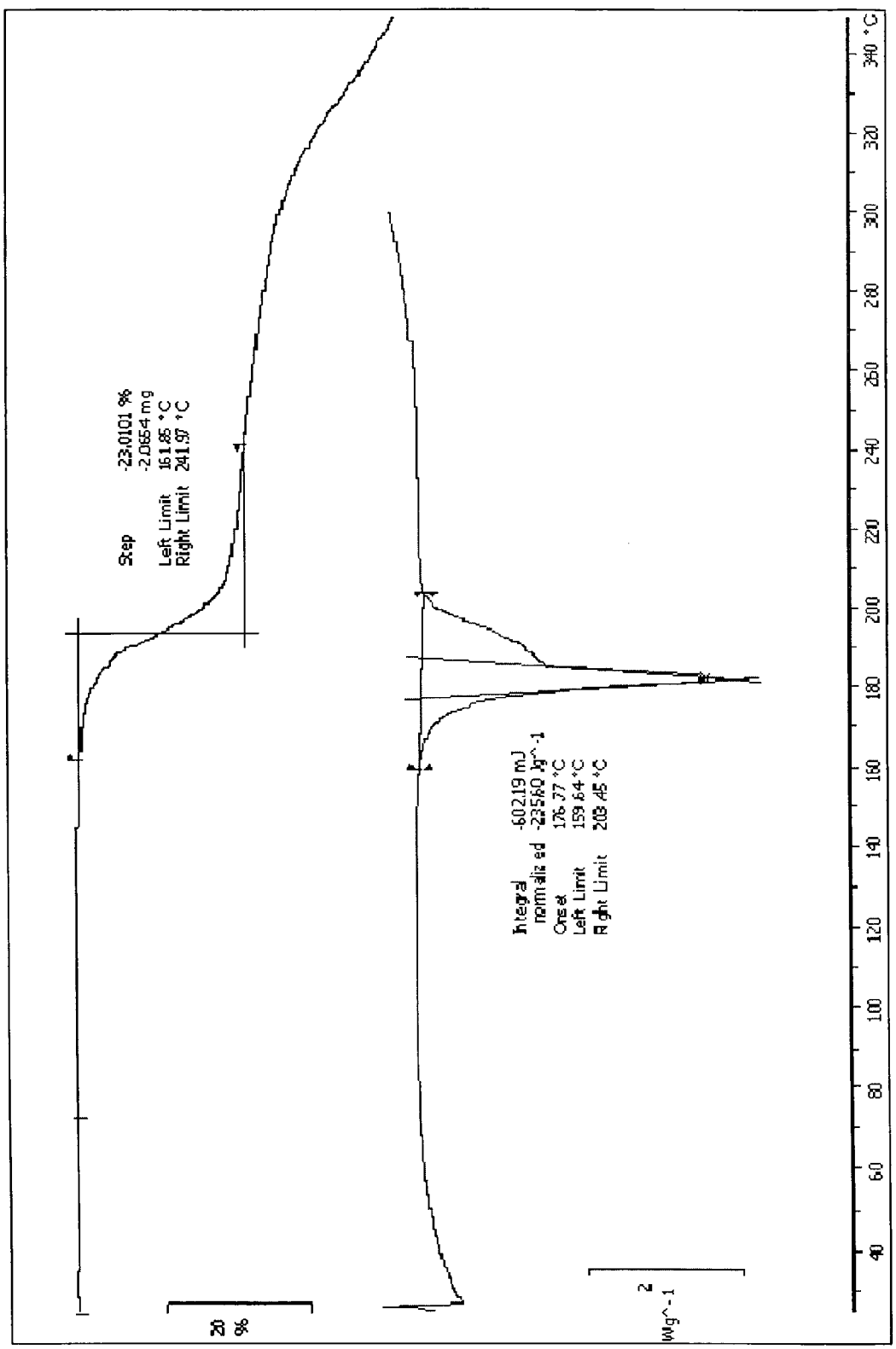
FIG. 18 shows the results of TGA (top) and DSC (bottom) of the Batch Citrate 1.
Figure 19:
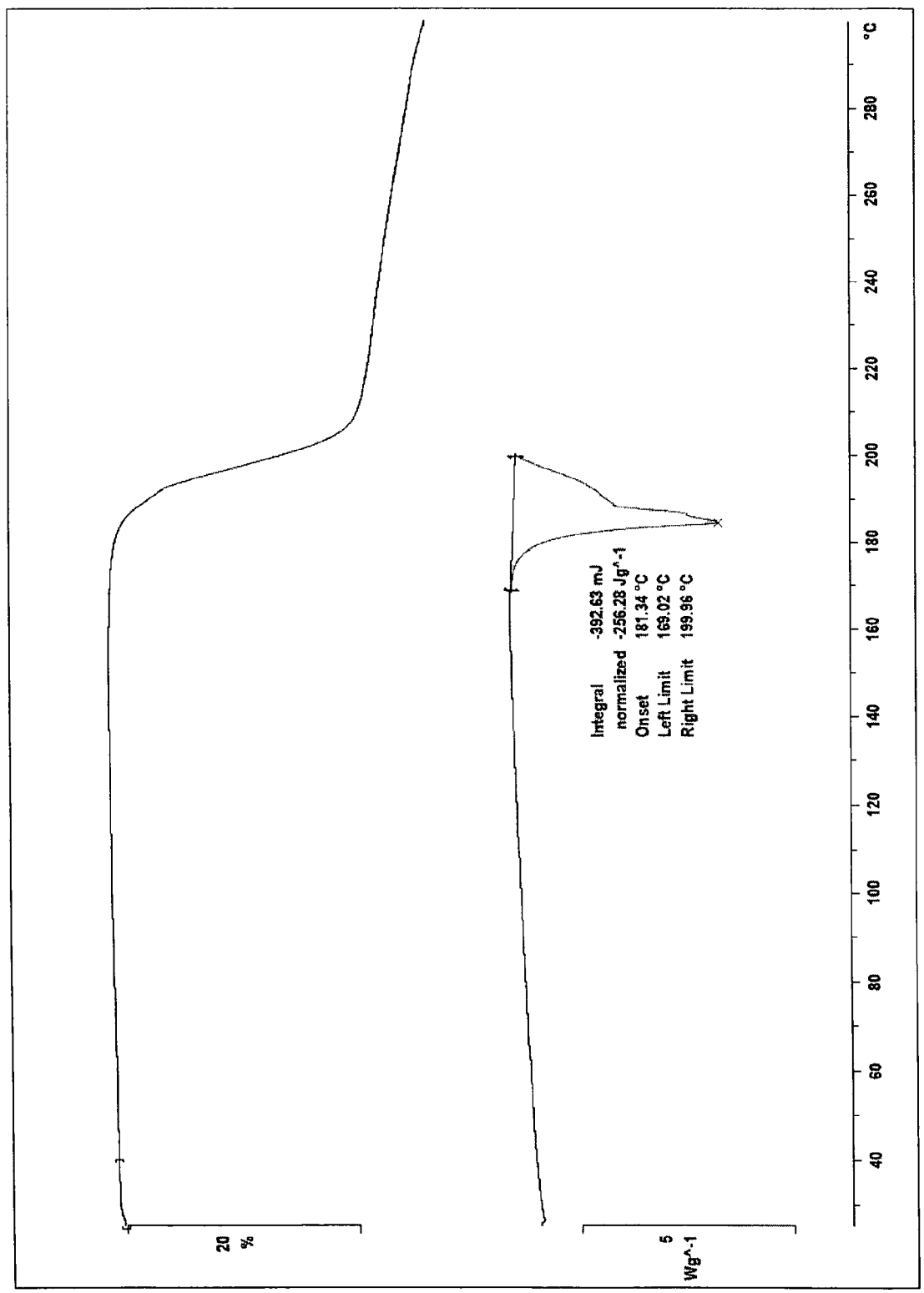
FIG. 19 shows the results of TGA (top) and DSC (bottom) of the Batch Citrate 2.
Figure 20:
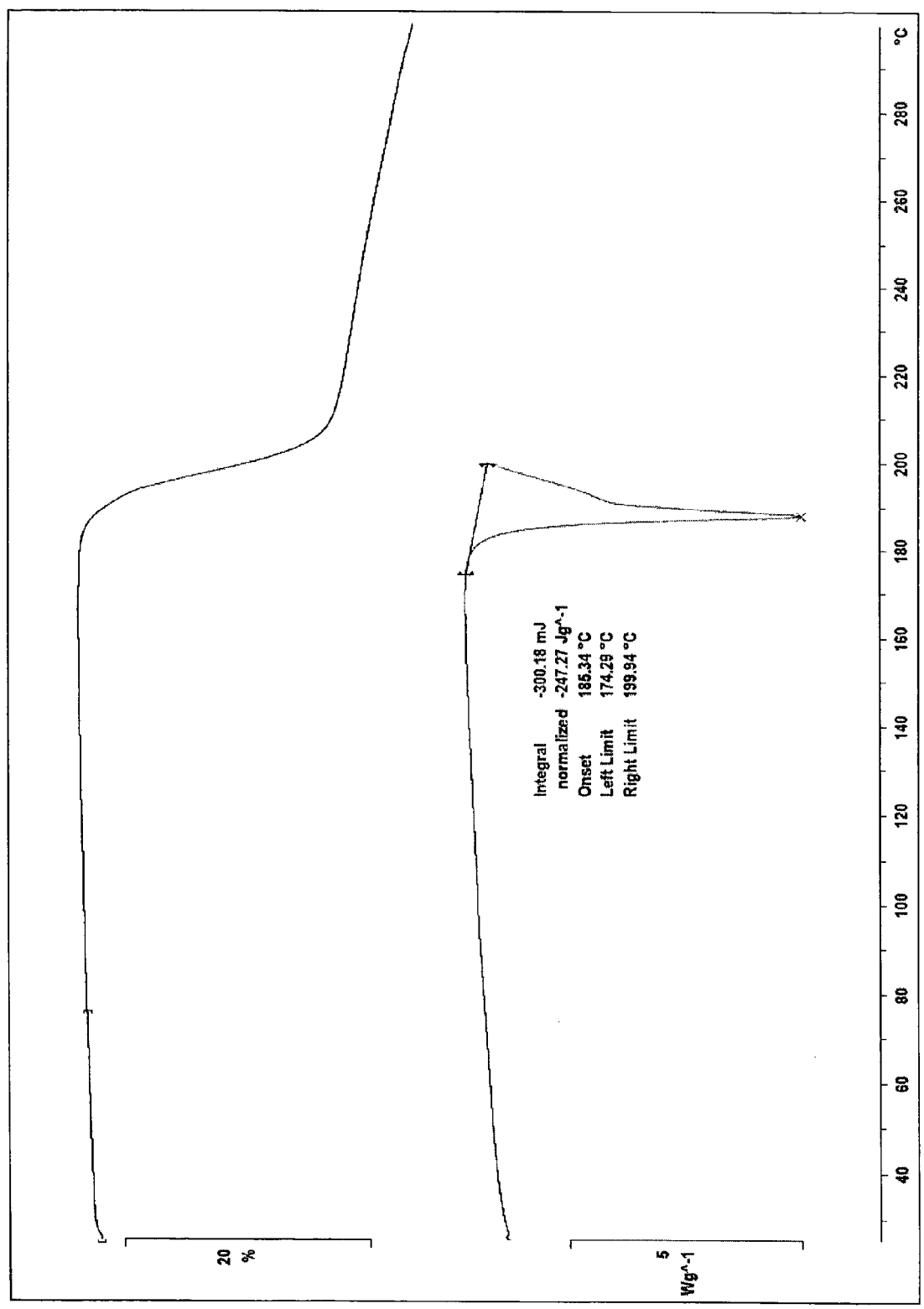
FIG. 20 shows the results of TGA (top) and DSC (bottom) of the Batch Citrate 3.
Figure 21:
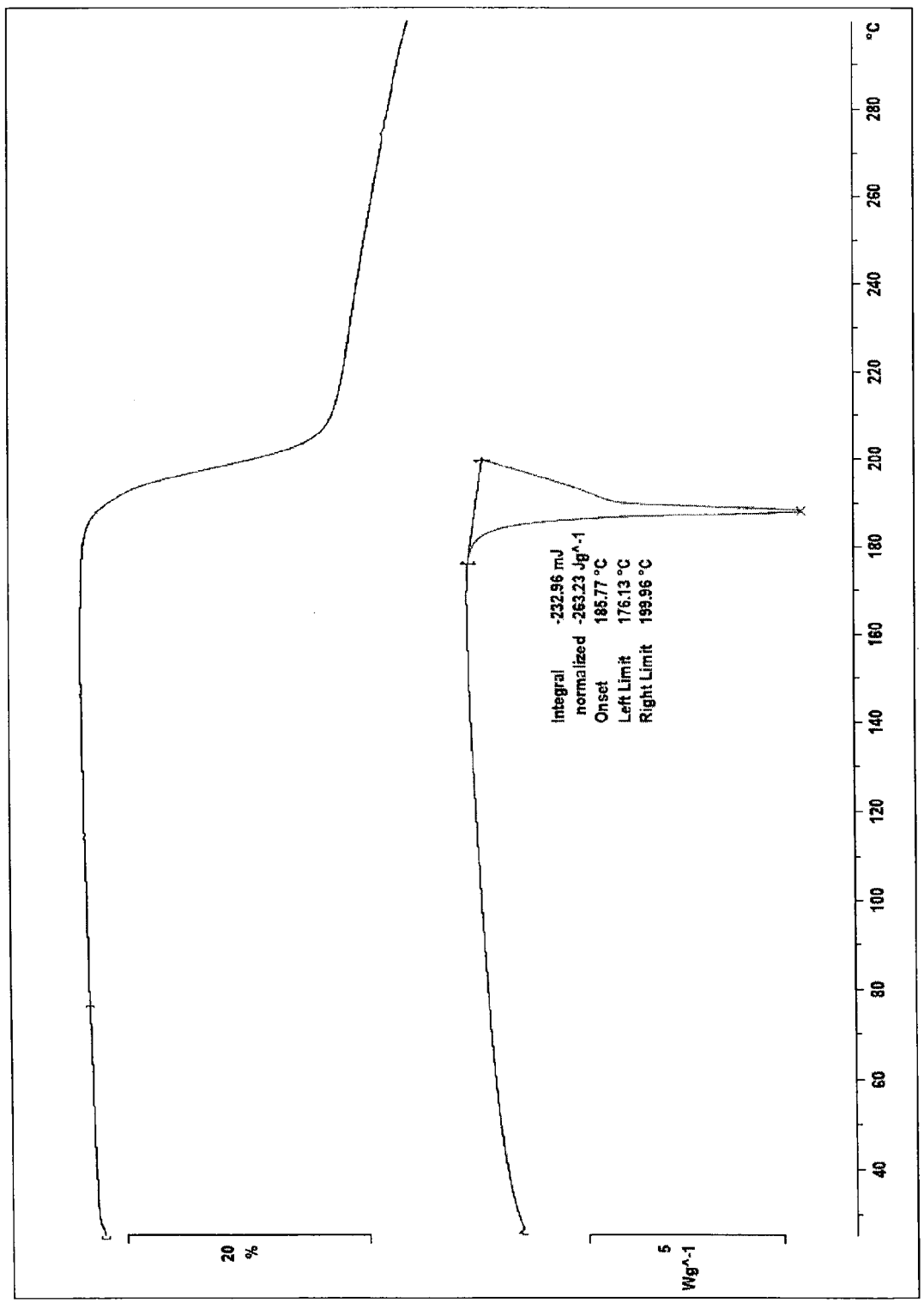
FIG. 21 shows the results of TGA (top) and DSC (bottom) of the Batch Citrate 4.

FIG. 17 shows the high resolution X-ray diffraction patterns (D5000) of Batches Citrates 1, 2, 3 and 4 with Citrate 1 employed as a reference standard. It is quite clear that the batches are very similar indeed and essentially identical for the purposes of establishing solid form classification. A complete listing of all peaks observed is shown in table 5.

FIGS. 18, 19, 20 and 21 show the TGA (top) and DSC (bottom) spectra for Batches Citrate 1, 2, 3 and 4, respectively. The thermal gravimetric analysis clearly demonstrates that the citrate salts show no weight loss until they melt with to decomposition at 180° C. This indicates the general temperature stability and robust nature of the citrate salt and also that it is generally not hygroscopic. In addition inspection of the differential scanning calorimetry plot indicates that no other events (phase changes, etc) are evident for these salts. It is also clear from this data that the batches are essentially identical in their thermal profiles.

Figure 22:
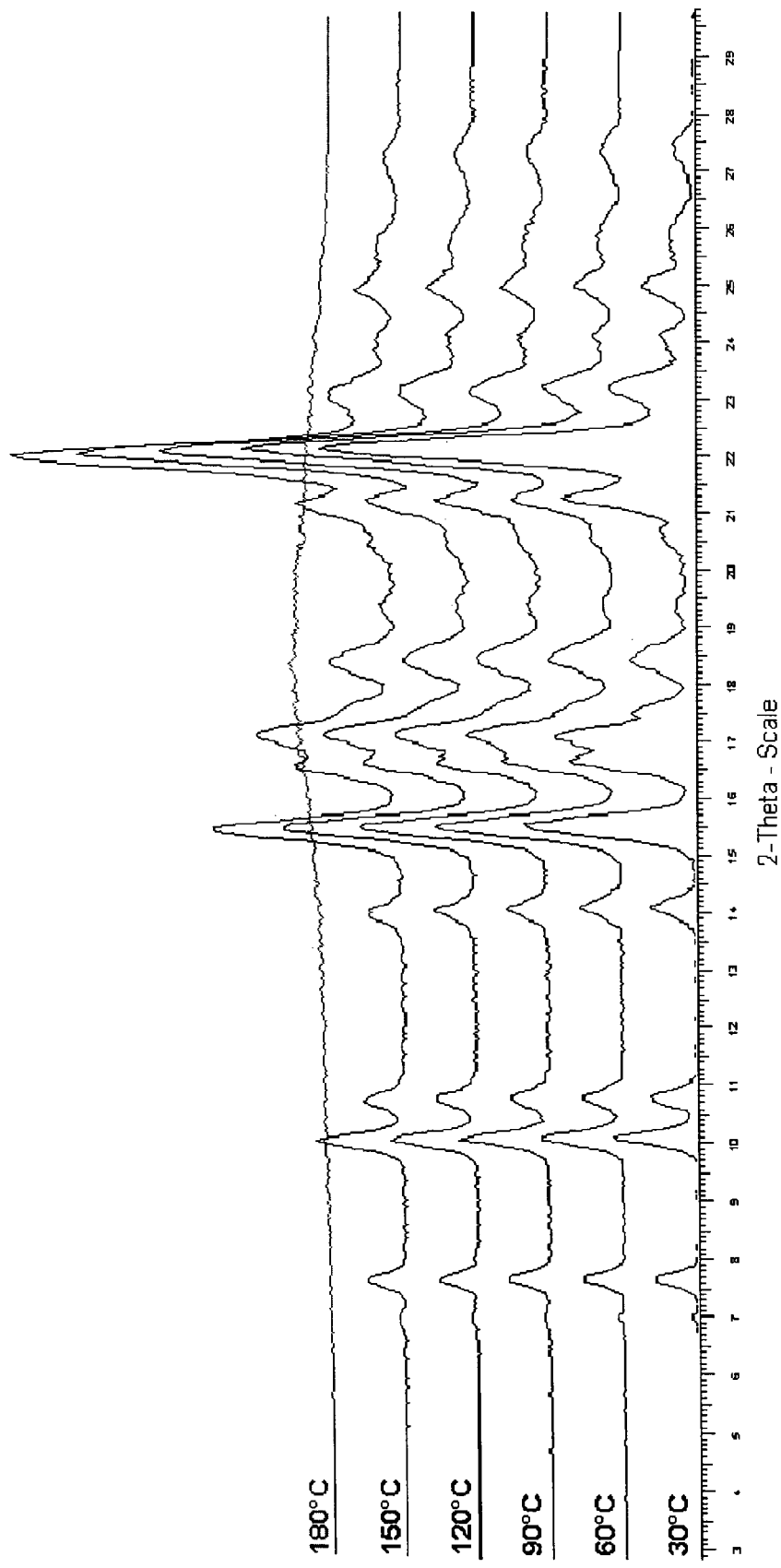
FIG. 22 shows the variable temperature X-ray diffraction pattern of Batch Citrate 1.
Figure 23:
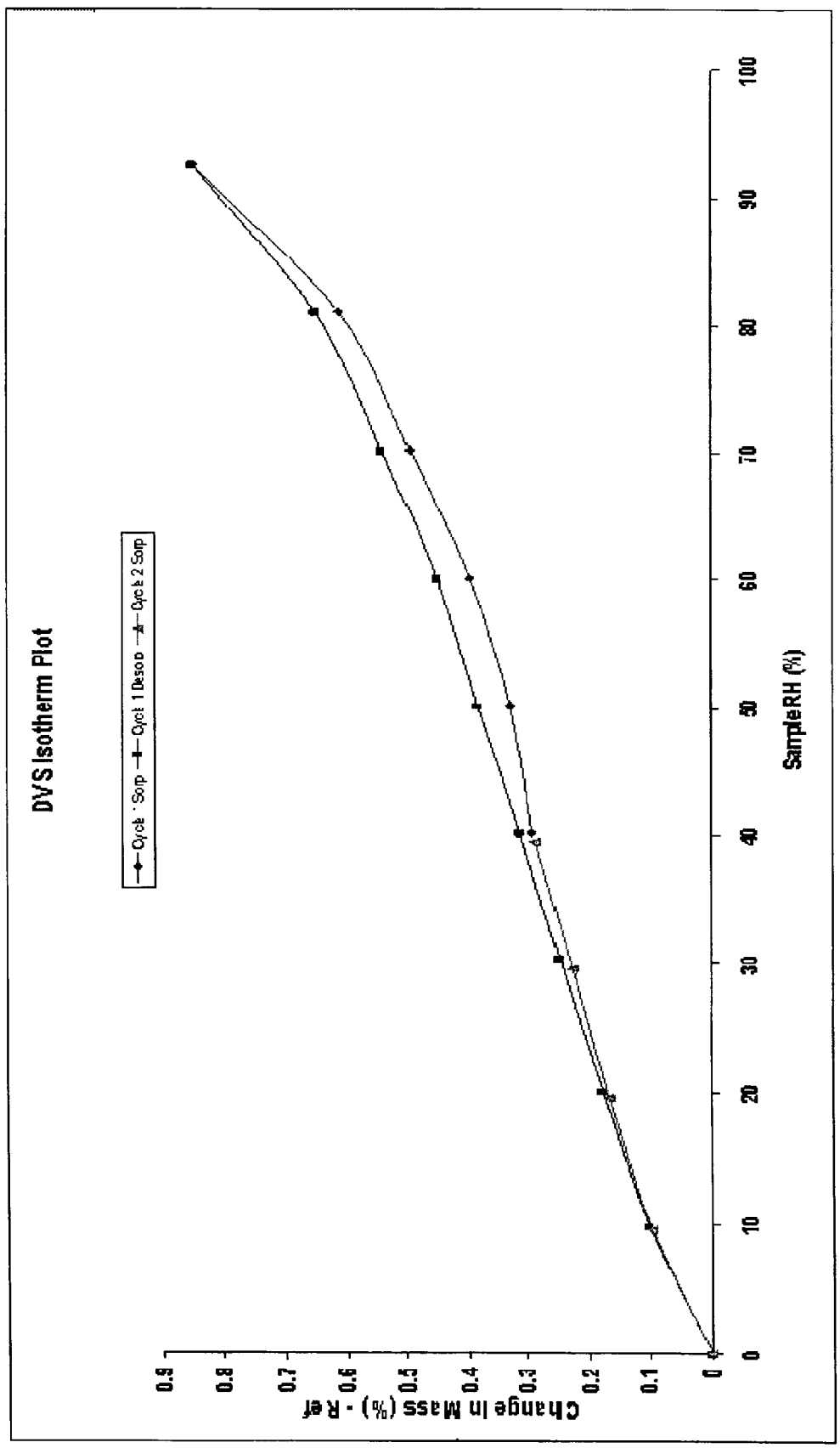
Figure 25:
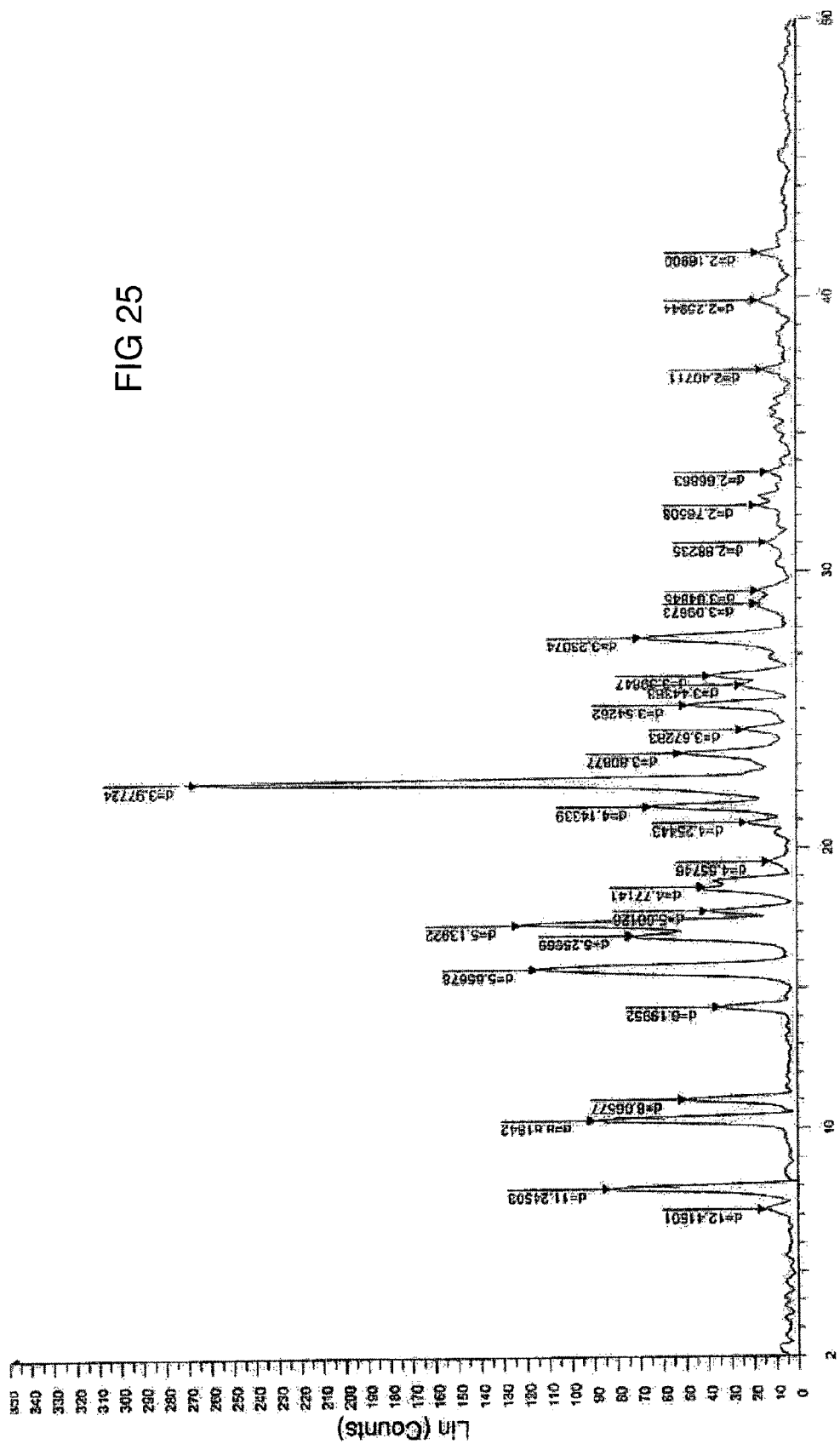
FIGS. 25, 26, 27, 28 and 29 show the high resolution X-ray diffraction pattern of Batches Citrate 2, 3, 4, 5 and 6 respectively, recorded on a different instrument from that of FIG. 17.
Figure 26:
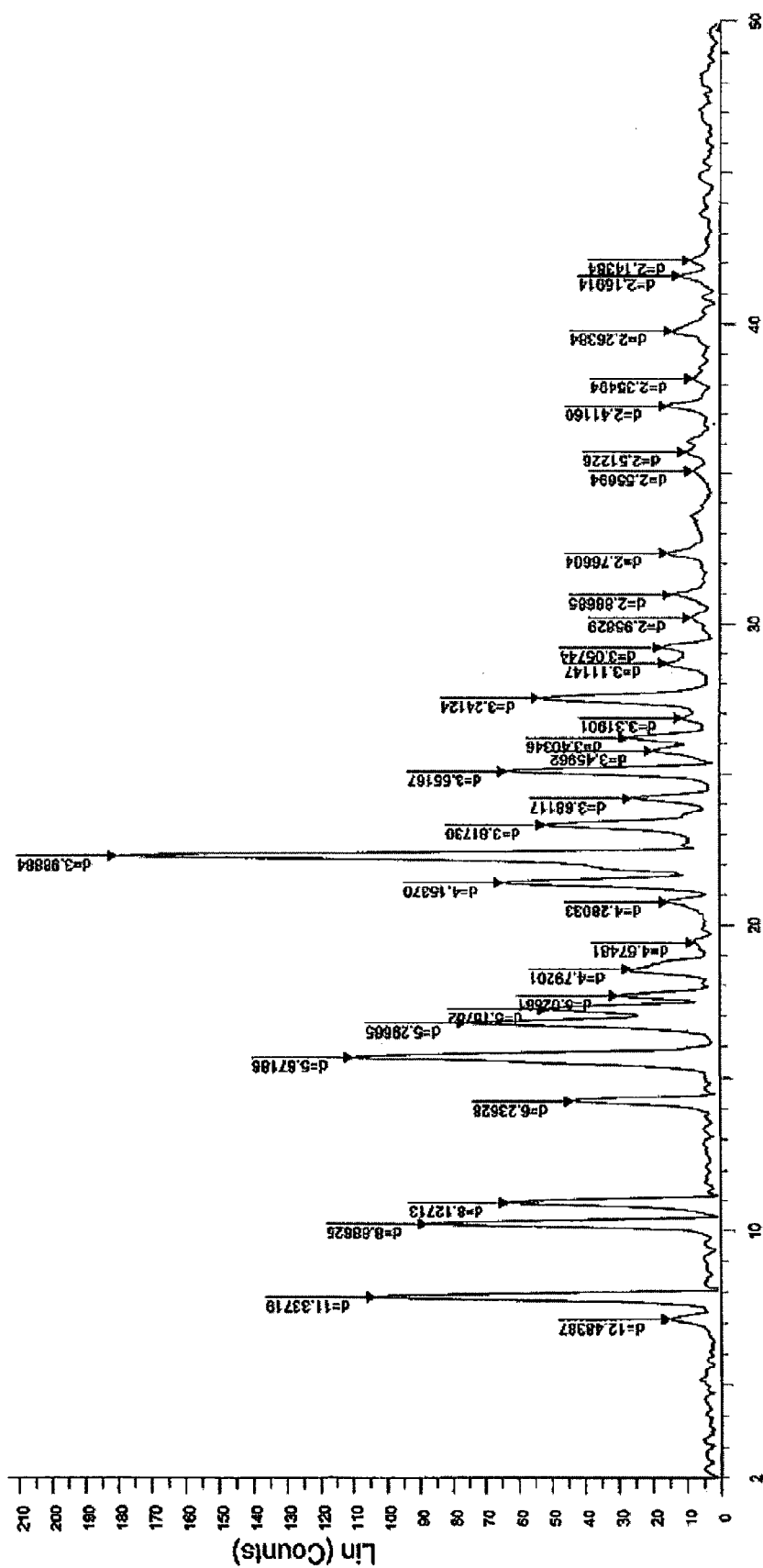
Figure 27:
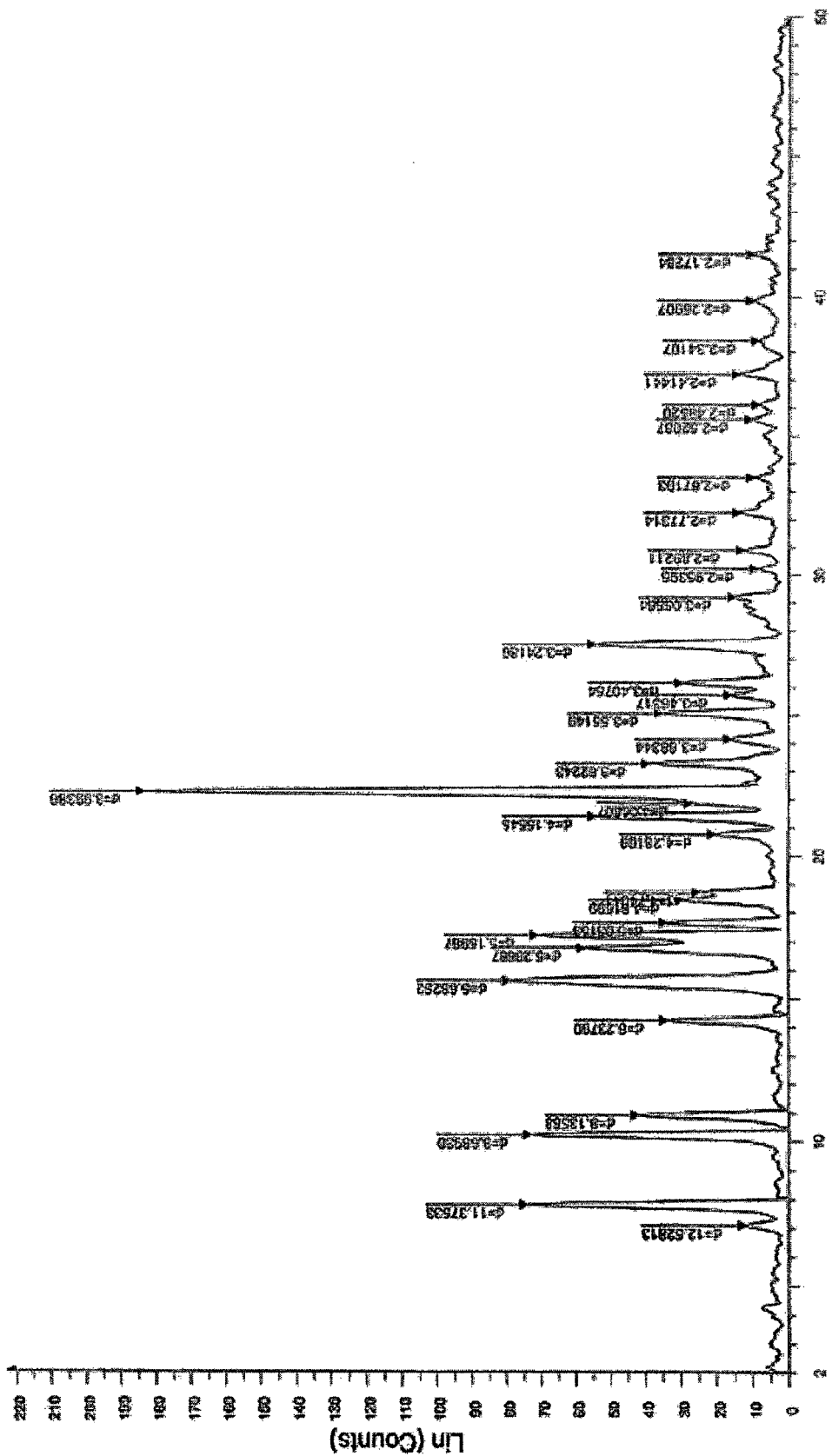
Figure 28:
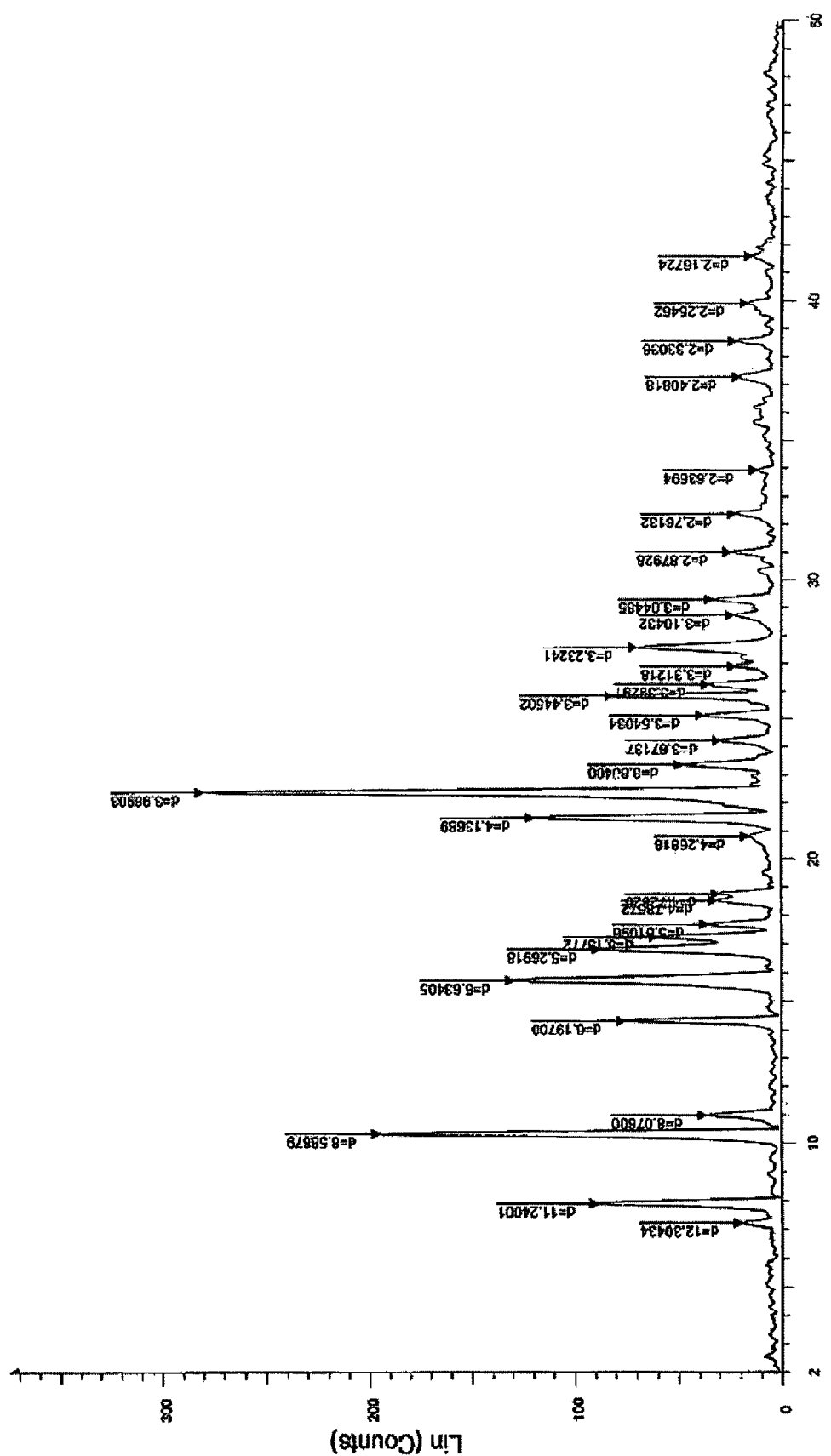
Figure 29:
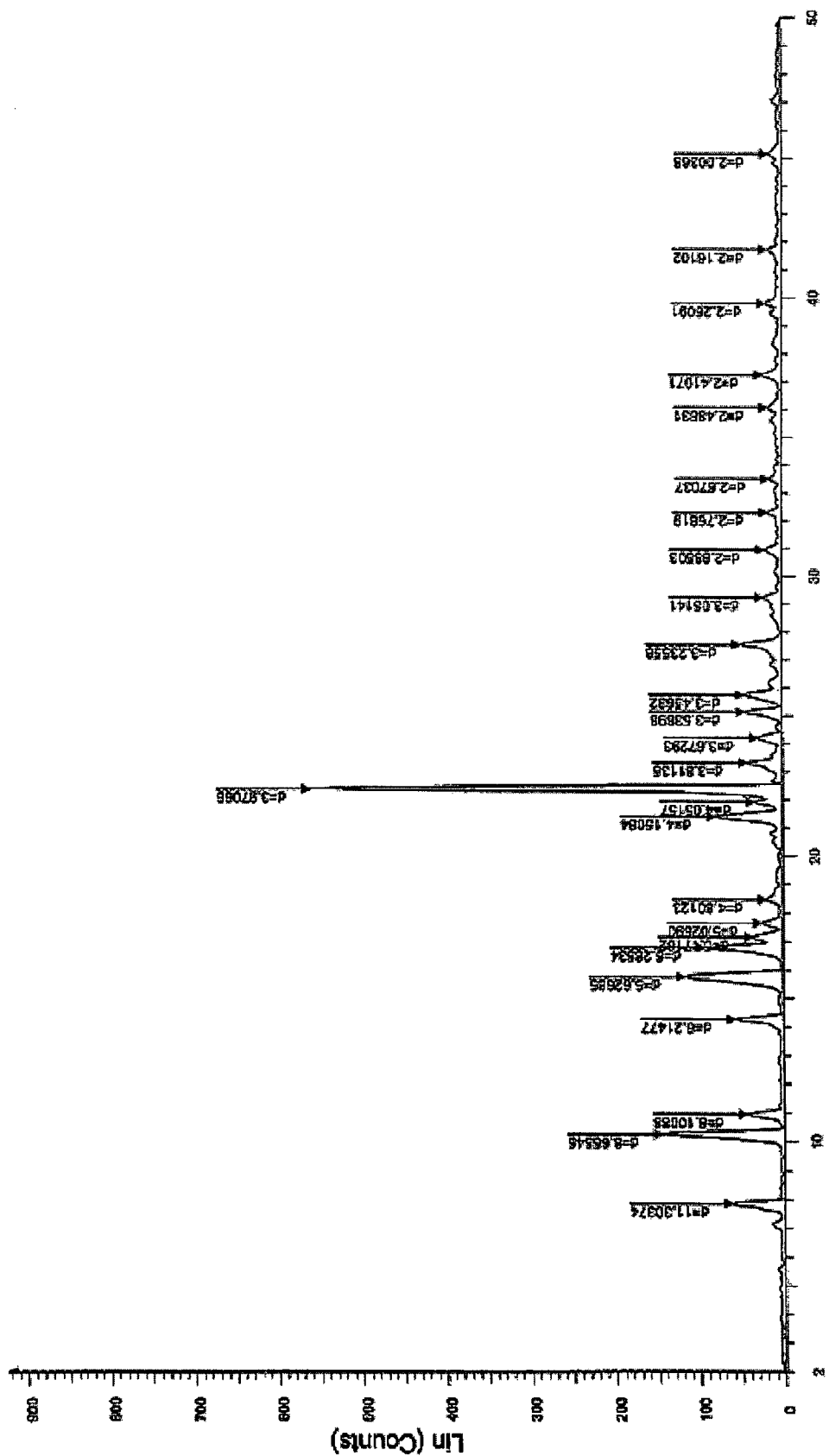

FIG. 22 shows the variable temperature X-ray diffraction pattern of Batch Citrate 1. With reference to the variable temperature X-ray diffraction patterns shown it is notable that there is no change irrespective of the temperature of the experiment once again indicating the robust nature of the citrate salt. In addition, FIGS. 23 and 24 show the GVS experiment and post-GVS XRPD spectra, respectively. The data indicate that Batch Citrate 1 also has low hygroscopicity, and no significant amount of water (less than 0.8%) is taken up between 0 and 90% RH. There is no change in the XRPD pattern before and after the GVS experiment.

FIGS. 25, 26, 27, 28 and 29 show the high resolution X-ray diffraction pattern of Batches Citrate 2, 3, 4, 5 and 6, respectively, recorded on a different instrument from that of FIG. 17. This data is of a very good resolution with expansion of the peaks in the y-axis as compared to FIG. 17, however clearly the reflections are occurring at essentially identical 2theta and relative intensities to that of the other XRPD data presented herein.

In order to determine the propensity of polymorphism for the citrate salt the group A material was maturated in 27 different solvents. A small amount of solid was slurried with the corresponding solvent (see Table 4 below) and stored in the incubator and subjected to 4 h-heat/cool cycles at 50° C./r.t. for 24 h. The solvents were then removed under vacuum, and the remaining solids analysed by XRPD. In all cases only one solid form was identified.

TABLE 4

Results of solid analysis after maturation studies

| Solvent | Solid Form | Solvent | Solid Form | Solvent | Solid Form |
|---|---|---|---|---|---|
| Heptane | Form A | 3-methyl-1-butanol | Form A | Ethanol | Form A |
| Cyclohexane | Form A | Methyl iso-butyl ketone | Form A | Isopropyl acetate | Form A |
| 1,4-dioxane | Form A | 2-butanol | Form A | methanol | Form A |
| Toluene | Form A | 2-methoxy ethanol | Form A | Acetonitrile | Form A |
| TBME | Form A | 1-butanol | Form A | Nitromethane | Form A |
| Isobutyl acetate | Form A | IPA | Form A | DMSO | Form A |
| Propyl acetate | Form A | Methylethyl ketone | Form A | Water | Form A |
| Ethyl acetate | Form A | 1-propanol | Form A | Tetrahydro furan | Form A |
| 1-pentanol | Form A | acetone | Form A | Dicloromethane | Form A |

The stability of the citrate salt group A material was tested in harsher conditions, when the samples were kept for a week in a humidity chamber at 60° C. and 96% RH. FIG. 30 shows that no changes are observed in the crystalline pattern to even under these conditions.

TABLE 5

List of significant X-ray diffraction peaks for the citrate salt (Batch Citrate 6 with 2theta ranges derived from Batches Citrate 2-5)

| Position of Peak (2-theta °, ±0.5°) | Relative intensity |
| --- | --- |
| 7.1 | Weak |
| 7.8 | Medium |
| 10.2 | Strong |
| 10.9 | Weak |
| 14.2 | Medium |
| 15.7 | Medium |
| 16.8 | Medium |
| 17.1 | Weak |
| 17.6 | Weak |
| 18.5 | Weak |
| 18.7 | Weak |
| 20.7 | Weak |
| 21.4 | Medium |
| 22.4 | Strong |
| 23.3 | Weak |
| 24.2 | Weak |
| 25.1 | Weak |
| 25.8 | Weak |
| 26.2 | Weak |
| 26.9 | Weak |
| 27.5 | Weak |
| 28.7 | Weak |
| 29.3 | Weak |
| 31.0 | Weak |
| 32.4 | Weak |
| 37.3 | Weak |
| 38.6 | Weak |
| 39.9 | Weak |
| 41.6 | Weak |

As can be seen the citrate salt may be characterised by showing on X-ray diffraction a peak on the 2theta scale at 22.4°±0.5°

In some embodiments the citrate salt may be further characterised as showing on X-ray diffraction peaks on the 2theta scale at 10.2°±0.5° and 15.7°±0.5°.

In some embodiments the citrate salt may be further characterised as showing on X-ray diffraction at least four peaks on the 2theta scale selected from the to group consisting of 7.8°±0.5°, 10.2°±0.5°, 14.2°±0.5°, 15.7°±0.5°, 16.8°±0.5°, 21.4°±0.5°, and 22.4°±0.5°.

In some embodiments the citrate salt may be further characterised as showing on X-ray diffraction at least 6 peaks on the 2theta scale selected from the group consisting of 7.8°±0.5°, 10.2°±0.5°, 14.2°±0.5°, 15.7°±0.5°, 16.8°±0.5°, 21.4°±0.5°, and 22.4°±0.5°.

In some embodiments the citrate salt may be further characterised as showing on X-ray diffraction peaks on the 2theta scale at 7.8°±0.5°, 10.2°±0.5°, 14.2°±0.5°, 15.7°±0.5°, 16.8°±0.5°, 21.4°±0.5°, and 22.4°±0.5°.

In some embodiments the citrate salt may be further characterised as showing on X-ray diffraction peaks on the 2theta scale at 10.9°±0.5°, 17.1°±0.5°, 23.3°±0.5°, 25.1°±0.5°, 25.8°±0.5°, and 27.5°±0.5°.

Whilst the peaks discussed above are the characteristic peaks the citrate salt may also shows on X-ray diffraction peaks on the 2theta scale at 7.2°±0.5°, 17.6°±0.5°, 18.5°±0.5°, 18.7°±0.5°, 20.7°±0.5°, 23.1°±0.5°, 24.2°±0.5°, 26.2°±0.5°, 26.9°±0.5°, 28.7°±0.5°, 29.3°±0.5°, 31.0°±0.5°, 32.4°±0.5°, 37.3°±0.5°, 38.6°±0.5°, 39.9°±0.5° and 41.6°±0.5°.

As will be appreciated by a skilled worker in the field the relative intensities of the diffractions can vary depending upon a number of factors such as the method of the sample preparation and the type of instrument used. In addition in certain instances some of the peaks referred to above may not be detectable.

The salt of the present invention may be produced by reaction of the free base of compound (I) with an appropriate form of citric acid in an appropriate solvent and recovering from the reaction mixture the resultant salt after crystallisation, precipitation or evaporation.

The reaction to form the salt may be carried out in any non-interfering solvent, or mixture of solvents, in which the free base has appropriate solubility. Examples of suitable solvents of this type include toluene, tetrahydrofuran and water. The process typically involves dissolution of the free base in the appropriate solvent at elevated temperature, such as greater than 20° C. In some embodiments, eg tetrahydrofuran, the free base is dissolved in the solvent at a temperature of about 65° C. In some embodiments, eg water, the free base is dissolved in the solvent at a temperature of about 90° C.

Once the free base has been dissolved in the appropriate solvent the process then involves addition of a suitable amount of the acid. The amount of acid may vary although typically the amount of acid used is a stoichiometric equivalent or a slight stoichiometric excess. Following addition of the acid the process then typically involves stirring of the reaction mixture at the addition temperature for a period of 1 to hour followed by cooling of the reaction mixture to a temperature below the reaction temperature to facilitate crystallisation. Once the desired level of crystal formation has occurred the crystals may be isolated by filtration and dried using normal means in the art.

In another embodiment the present invention provides the use of the salts of the invention in the treatment of proliferative disorders. The formulations and methodology for the use of compounds of this type and the disorders that may be treated thereby are as disclosed in PCT/SG2006/000352.

The present invention will now be described with reference to the following non-limiting examples. Hydrochloride salts were prepared as discussed above for comparative examples and analysed in an analogous manner.

EXAMPLE 1

Formation of the Hydrochloride salt of Compound I

Comparative Example

The free base 11-(2-pyrrolidin-1-yl-ethoxy)-14,19-dioxa-5,7,26-triaza-tetracyclo[19.3.1.1(2,6).1(8,12)]heptacosa-1(25),2(26),3,5,8,10,12(27),16,21,23-decaene was dissolved in dichloromethane, brought to reflux and treated with activated carbon. The mixture was filtered hot through a pad of celite and washed with dichloromethane. To the filtrate was added methanolic HCl and the mixture was stirred at 10-15° C. for 2-3 hours. The slurry was cooled to 5-10° C., filtered, washed with heptane and dried in a vacuum oven at 40-45° C. to afford 11-(2-pyrrolidin-1-yl-ethoxy)-14,19-dioxa-5,7,26-triaza-tetracyclo[19.3.1.1(2,6).1(8,12)]heptacosa-1(25),2(26),3,5,8,10,12(27),16,21,23-decaene hydrochloride.

EXAMPLE 2

Formation of Citrate Salt

Compound I (50 mg, 0.106 mmol) was suspended in either THF or toluene (2 mL), and gently heated to 65° C. until it became a clear solution. The solution was then treated with 1 equivalent of citric acid, heated at 65° C. for one hour and slowly cooled down to 5° C. overnight to facilitate crystallisation. The crystals thus formed were then isolated by filtration.

EXAMPLE 3

Formation of Citrate Salt

Compound 1 (50 mg, 0.106 mmol) was suspended in THF (2 mL), and gently heated to 65° C. until it became a clear solution. The solution was then treated with 1 equivalent of citric acid (as a solution in water), heated at 90° C. for one hour and slowly cooled down to 5° C. overnight to facilitate crystallisation. The crystals thus formed were then isolated by filtration.

EXAMPLE 4

Thermal Gravimetric Analysis and Differential Scanning Calorimetry

The samples of both hydrochloride (comparative) and citrate salts were subjected to thermal gravimetric analysis and differential scanning calorimetry under the following conditions. DSC data were collected on a TA Instruments Q2000 equipped with a 50 position auto-sampler. The instrument was calibrated for energy and temperature calibration using certified indium. Typically 0.5-3 mg of each sample, in a pin-holed aluminium pan, was heated at 10° C.·min$^{-1}$ from 25° C. to 270° C.

A nitrogen purge of 50 ml·min$^{-1}$ was maintained over the sample. The instrument control software was Thermal Advantage v4.6.6 and the data were analysed using Universal Analysis v4.3A. Alternatively, DSC data were collected on a Mettler DSC 823e equipped with a 50 position auto-sampler. The instrument was calibrated for energy and temperature using certified indium. Typically 0.5-3 mg of each sample, in a pin-holed aluminium pan, was heated at 10° C.·min$^{-1}$ from 25° C. to 270° C. A nitrogen purge at 50 ml·min$^{-1}$ was maintained over the sample. The instrument control and data analysis software was STARe v9.01.

TGA data were collected on a TA Instruments Q500 TGA, equipped with a 16 position auto-sampler. The instrument was temperature calibrated using certified Alumel. Typically 5-30 mg of each sample was loaded onto a pre-tared platinum crucible and aluminium DSC pan, and was heated at 10° C.·min$^{-1}$ from ambient temperature to 300° C. A nitrogen purge at 60 ml·min$^{-1}$ was maintained over the sample. The instrument control software was Thermal Advantage v4.6.6 and the data were analysed using Universal Analysis v4.3A. Alternatively, TGA data were collected on a Mettler TGA/SDTA 851e equipped with a 34 position auto-sampler. The instrument was temperature calibrated using certified indium. Typically 5-30 mg to of each sample was loaded onto a pre-weighed aluminium crucible and was heated at 10° C.·min$^{-1}$ from ambient temperature to 300° C. A nitrogen purge at 50 ml·min$^{-1}$ was maintained over the sample. The instrument control and data analysis software was STARe v9.01. The results of the scans are shown in the figures discussed above.

EXAMPLE 5

X-Ray Diffraction Analysis

The samples of both hydrochloride (comparative) and citrate salts were subjected to X-ray diffraction to determine the characteristic X-ray diffraction pattern. The conditions used were as follows: X-Ray Powder Diffraction patterns were collected on a Siemens D5000 diffractometer using Cu Kα radiation (40 kV, 40 mA), θ-θ goniometer, divergence of V20 and receiving slits, a graphite secondary monochromator and a scintillation counter. The instrument is performance checked using a certified Corundum standard (NIST 1976).

Ambient Conditions

Samples run under ambient conditions were prepared as flat plate specimens using powder as received. Approximately 35 mg of the sample was gently packed into a cavity cut into polished, zero-background (510) silicon wafer. The sample was rotated in its own plane during analysis. The details of the data collection are:

Angular range: 2 to 42 °2θ
Step size: 0.05 °2θ
Collection time: 4 s·step$^{-1}$.

Alternatively, X-Ray Powder Diffraction patterns were collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consists of a single Göbel multilayer mirror coupled with a pinhole collimator of 0.3 mm. The beam divergence, i.e. the effective size of the X-ray beam on the sample, was approximately 4 mm. A θ-θ continuous scan mode was employed with a sample-detector distance of 20 cm which gives an effective 2θ range of 3.2°-29.7°. Typically the sample would be exposed to the X-ray beam for 120 seconds.

Samples run under ambient conditions were prepared as flat plate specimens using powder as received without grinding. Approximately 1-2 mg of the sample was lightly pressed on a glass slide to obtain a flat surface.

Non-Ambient Conditions

Samples run under non-ambient conditions were mounted on a silicon wafer with heat-conducting compound. The sample was then heated to the appropriate temperature at ca. 10° C.·min$^{-1}$ and subsequently held isothermally for ca 2 minutes before data collection was initiated.

The X-ray diffraction patterns for the citrate salts are shown in the figures discussed above.

EXAMPLE 6

Variable Temperature X-Ray Diffraction

In order to probe the stability of the samples of the citrate salts variable temperature X-ray diffraction was carried out. Thus, the salts were scanned under X-ray diffraction conditions at a series of temperatures and the characteristic peaks determined. The results of each of the scans are shown in the figures discussed above.

The details of specific embodiments described in this invention are not to be construed as limitations. Various equivalents and modifications may be made without departing from the essence and scope of this invention, and it is understood that such equivalent embodiments are part of this invention.

What is claimed is:
1. A crystalline citrate salt of 11-(2-pyrrolidin-1-ylethoxy)-14,19-dioxa-5,7,26-triaza-tetracyclo[19.3.1.1(2,6).1(8,12)]heptacosa-1(25),2(26),3,5,8,10,12(27),16,21,23-decaene which shows on X-ray diffraction a peak on the 2theta scale at 22.4°±0.5°.

2. A salt according to claim 1 wherein the salt is the 1:1 salt.

3. A salt according to claim 1 which also shows on X-ray diffraction peaks on the 2theta scale at 10.2°±0.5° and 15.7°±0.5°.

4. A salt according to claim 1 which shows on X-ray diffraction at least four peaks on the 2theta scale selected from the group consisting of 7.8°±0.5°, 10.2°±0.5°, 14.2°±0.5°, 15.7°±0.5°, 16.8°±0.5°, 21.4°±0.5°, and 22.4°±0.5°.

5. A salt according to claim 4 which shows on X-ray diffraction at least 6 peaks on the 2theta scale selected from the group consisting of 7.8°±0.5°, 10.2°±0.5°, 14.2°±0.5°, 15.7°±0.5°, 16.8°±0.5°, 21.4°±0.5°, and 22.4°±0.5°.

6. A salt according to claim 4 which shows on X-ray diffraction peaks on the 2theta scale at 7.8°±0.5°, 10.2°±0.5°, 14.2°±0.5°, 15.7°±0.5°, 16.8°±0.5°, 21.4°±0.5°, and 22.4°±0.5°.

7. A salt according to claim 6 which also shows on X-ray diffraction peaks on the 2theta scale at 10.9°±0.5°, 17.1°±0.5°, 23.3°±0.5°, 25.1°±0.5°, 25.8°±0.5°, and 27.5°±0.5°.

8. A salt according to claim 7 which also shows on X-ray diffraction peaks on the 2theta scale at 7.2°±0.5°, 17.6°±0.5°, 18.5°±0.5°, 18.7°±0.5°, 20.7°±0.5°, 23.1°±0.5°, 24.2°±0.5°, 26.2°±0.5°, 26.9°±0.5°, 28.7°±0.5°, 29.3°±0.5°, 31.0°±0.5°, 32.4°±0.5°, 37.3°±0.5°, 38.6°±0.5°, 39.9°±0.5° and 41.6°±0.5°.

9. A pharmaceutical composition comprising a salt according to claim 1.

10. A method of treating cancer comprising administration of a therapeutically effective amount of a salt according to claim 1 to a patient in need thereof, wherein the cancer is selected from the group consisting of colon cancer, acute myeloid leukaemia and myelofibrosis.

11. A method according to claim 10 wherein the cancer is colon cancer.

12. A method according to claim 10 wherein the cancer is acute myeloid leukaemia.

13. A method according to claim 10 wherein the cancer is myelofibrosis.

* * * * *